United States Patent
Schaeffer et al.

(10) Patent No.: US 8,945,142 B2
(45) Date of Patent: Feb. 3, 2015

(54) DELIVERY SYSTEM FOR IMPLANTING NASAL VENTILATION TUBE

(75) Inventors: Darin Schaeffer, Bloomington, IN (US);
Patrick C. Melder, Marietta, GA (US);
Kathryn Evert, Bloomington, IN (US);
Cleve Koehler, Ellettsville, IN (US);
Kem Hawkins, Bloomington, IN (US);
Thomas Cherry, Covington, LA (US);
Chase Wooley, Floyds Knobs, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 865 days.

(21) Appl. No.: 13/158,063

(22) Filed: Jun. 10, 2011

(65) Prior Publication Data
US 2012/0150119 A1 Jun. 14, 2012

Related U.S. Application Data

(63) Continuation-in-part of application No. 13/059,531, filed as application No. PCT/US2009/055252 on Aug. 27, 2009.

(60) Provisional application No. 61/092,269, filed on Aug. 27, 2008.

(51) Int. Cl.
*A61F 9/00* (2006.01)
*A61B 17/34* (2006.01)
(Continued)

(52) U.S. Cl.
CPC ........ *A61M 16/0666* (2013.01); *A61B 17/3468* (2013.01); *A61M 16/0463* (2013.01)
USPC ....... 606/108; 606/162; 606/185; 604/164.01

(58) Field of Classification Search
CPC ......... A61F 11/002; A61F 11/00; A61F 2/82; A61F 2/186; A61F 11/004; A61F 11/08; A61F 2/18; A61F 2/2466; A61F 2002/30675; A61F 2002/9517; A61F 2002/9522; A61F 2/0095; A61F 2/95; A61B 17/24; A61B 17/3468; A61B 1/233; A61B 2017/00787; A61B 17/16; A61M 2210/0618; A61M 2210/0681; A61M 2210/0662; A61M 2210/0668
USPC ................ 606/108, 109, 140, 191, 192, 199; 623/1.11, 1.19, 1.23; 604/164.01, 604/164.06
See application file for complete search history.

(56) References Cited

U.S. PATENT DOCUMENTS
3,530,860 A 9/1970 Majoros
(Continued)

FOREIGN PATENT DOCUMENTS
EP 2522386 11/2012
(Continued)

OTHER PUBLICATIONS
ATOS Medical, Sinoject, screenshot of product information taken from Atos Medical company website (http://www.atosmedical.com/For_professionals/Focus_areas/~/media/Sweden/MC0766-NoEN.pdf) visited on Aug. 19, 2013.
(Continued)

*Primary Examiner* — Kevin C Sirmons
*Assistant Examiner* — William Carpenter
(74) *Attorney, Agent, or Firm* — Buchanan Nipper

(57) ABSTRACT

Delivery systems and methods of creating an accessory maxillary ostium and implanting a ventilation tube for purposes of ventilation, irrigation, infusion or procedural work are described. The delivery systems include an introducer and an associated ventilation tube. An irrigation and/or infusion catheter may be advanced through the ventilation tube in order to irrigate or express the contents of the sinus cavities. A secondary irrigation and/or infusion catheter or a balloon catheter may be advanced through an outer irrigation and/or infusion catheter, deeply into the sinus cavity, in order to irrigate or express the contents of the sinus cavities. Moreover, the balloon catheter may alternatively or additionally be employed to for dilation of the natural ostium. Still further, a device for delivering drugs, fluids or the like, may be coupled to the ventilation tube for delivery of same.

14 Claims, 24 Drawing Sheets

(51) Int. Cl.
*A61F 11/00* (2006.01)
*A61M 5/178* (2006.01)
*A61M 16/06* (2006.01)
*A61M 16/04* (2006.01)

(56) References Cited

U.S. PATENT DOCUMENTS

| | | | |
|---|---|---|---|
| 3,888,258 A * | 6/1975 | Akiyama | 606/109 |
| 3,913,584 A * | 10/1975 | Walchle et al. | 606/109 |
| 4,174,716 A | 11/1979 | Treace | |
| 4,248,214 A | 2/1981 | Hannah et al. | |
| 4,403,611 A | 9/1983 | Babbitt et al. | |
| 4,473,073 A | 9/1984 | Darnell | |
| D276,937 S | 12/1984 | Griggs | |
| 4,568,337 A | 2/1986 | Treharne, III et al. | |
| 4,637,396 A | 1/1987 | Cook | |
| 4,650,488 A * | 3/1987 | Bays et al. | 623/23.64 |
| 4,695,275 A | 9/1987 | Bruce et al. | |
| 4,737,141 A | 4/1988 | Spits | |
| 4,747,405 A | 5/1988 | Leckrone | |
| 4,888,017 A | 12/1989 | DeVore et al. | |
| 4,964,850 A | 10/1990 | Bouton et al. | |
| 5,012,809 A | 5/1991 | Shulze | |
| 5,026,366 A | 6/1991 | Leckrone | |
| 5,026,378 A | 6/1991 | Goldsmith, III | |
| 5,032,123 A | 7/1991 | Katz et al. | |
| 5,053,040 A | 10/1991 | Goldsmith, III | |
| 5,139,502 A | 8/1992 | Berg et al. | |
| 5,167,686 A | 12/1992 | Wong | |
| 5,172,701 A * | 12/1992 | Leigh | 600/566 |
| 5,246,455 A | 9/1993 | Shikani | |
| 5,254,120 A | 10/1993 | Cinberg et al. | |
| 5,263,952 A | 11/1993 | Grace et al. | |
| 5,342,296 A * | 8/1994 | Persson et al. | 604/540 |
| 5,456,680 A | 10/1995 | Taylor et al. | |
| 5,466,239 A * | 11/1995 | Cinberg et al. | 606/109 |
| 5,496,329 A * | 3/1996 | Reisinger | 606/109 |
| 5,496,338 A | 3/1996 | Miyagi et al. | |
| 5,643,280 A * | 7/1997 | Del Rio et al. | 606/109 |
| 5,645,562 A | 7/1997 | Haan et al. | |
| 5,649,932 A | 7/1997 | Fouin et al. | |
| 5,681,323 A * | 10/1997 | Arick | 606/108 |
| 5,791,341 A | 8/1998 | Bullard | |
| 5,976,072 A | 11/1999 | Greenberg | |
| 6,143,016 A | 11/2000 | Bleam et al. | |
| 6,206,870 B1 | 3/2001 | Kanner | |
| 6,379,323 B1 | 4/2002 | Patterson | |
| 6,527,780 B1 * | 3/2003 | Wallace et al. | 606/108 |
| 6,543,452 B1 | 4/2003 | Lavigne | |
| 6,770,080 B2 | 8/2004 | Kaplan et al. | |
| 7,125,404 B2 | 10/2006 | Levatter | |
| D534,216 S | 12/2006 | Makower et al. | |
| 7,235,099 B1 | 6/2007 | Duncavage | |
| 7,269,453 B2 | 9/2007 | Mogul | |
| 7,335,218 B2 * | 2/2008 | Wilson et al. | 606/185 |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,559,925 B2 | 7/2009 | Goldfarb et al. | |
| 7,591,830 B2 | 9/2009 | Rutter | |
| 7,641,644 B2 | 1/2010 | Chang et al. | |
| 7,645,272 B2 | 1/2010 | Chang et al. | |
| 7,648,367 B1 | 1/2010 | Makower et al. | |
| 7,654,997 B2 | 2/2010 | Makower et al. | |
| 7,678,099 B2 | 3/2010 | Ressemann et al. | |
| 7,704,259 B2 | 4/2010 | Kaplan et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,785,315 B1 | 8/2010 | Muni et al. | |
| 7,789,876 B2 | 9/2010 | Zikorus et al. | |
| 7,803,150 B2 | 9/2010 | Chang et al. | |
| 7,842,062 B2 | 11/2010 | Keith et al. | |
| 7,854,744 B2 | 12/2010 | Becker | |
| 7,879,001 B2 * | 2/2011 | Haffner et al. | 604/8 |
| 7,951,130 B2 | 5/2011 | Eaton et al. | |
| 7,951,135 B2 | 5/2011 | Eaton et al. | |
| 8,070,693 B2 | 12/2011 | Ayala et al. | |
| 8,100,933 B2 | 1/2012 | Becker | |
| 8,277,478 B2 | 10/2012 | Drontle et al. | |
| 8,282,667 B2 | 10/2012 | Drontle et al. | |
| 8,435,290 B2 | 5/2013 | Clifford et al. | |
| 8,574,240 B2 * | 11/2013 | Loushin et al. | 606/109 |
| 8,702,722 B2 * | 4/2014 | Shahoian | 606/109 |
| 8,795,290 B2 * | 8/2014 | Konstorum et al. | 606/109 |
| 2001/0037046 A1 | 11/2001 | Weinberger et al. | |
| 2003/0047189 A1 | 3/2003 | Kumar et al. | |
| 2003/0130460 A1 | 7/2003 | Freeman et al. | |
| 2004/0064150 A1 | 4/2004 | Becker | |
| 2004/0068299 A1 | 4/2004 | Laske et al. | |
| 2005/0027246 A1 | 2/2005 | Dion | |
| 2005/0143817 A1 * | 6/2005 | Hunter et al. | 623/11.11 |
| 2005/0245906 A1 | 11/2005 | Makower et al. | |
| 2006/0004286 A1 | 1/2006 | Chang et al. | |
| 2006/0063973 A1 * | 3/2006 | Makower et al. | 600/114 |
| 2006/0095066 A1 | 5/2006 | Chang et al. | |
| 2006/0106361 A1 | 5/2006 | Muni et al. | |
| 2006/0149308 A1 | 7/2006 | Melsheimer et al. | |
| 2006/0155304 A1 | 7/2006 | Kaplan et al. | |
| 2006/0173487 A1 | 8/2006 | Uflacker et al. | |
| 2006/0178621 A1 | 8/2006 | Constantz et al. | |
| 2006/0210605 A1 | 9/2006 | Chang et al. | |
| 2007/0129705 A1 | 6/2007 | Trombley et al. | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0191781 A1 | 8/2007 | Richards et al. | |
| 2007/0208252 A1 | 9/2007 | Makower | |
| 2007/0208301 A1 | 9/2007 | Evard et al. | |
| 2007/0250105 A1 | 10/2007 | Ressemann et al. | |
| 2007/0282305 A1 | 12/2007 | Goldfarb et al. | |
| 2007/0293727 A1 | 12/2007 | Goldfarb et al. | |
| 2008/0015472 A1 | 1/2008 | Ressemann et al. | |
| 2008/0015497 A1 | 1/2008 | Keith et al. | |
| 2008/0015540 A1 | 1/2008 | Muni et al. | |
| 2008/0015544 A1 | 1/2008 | Keith et al. | |
| 2008/0015626 A1 | 1/2008 | Keith et al. | |
| 2008/0033353 A1 | 2/2008 | Truitt et al. | |
| 2008/0036368 A1 | 2/2008 | Frampton et al. | |
| 2008/0091067 A1 | 4/2008 | Dollar | |
| 2008/0097154 A1 | 4/2008 | Makower et al. | |
| 2008/0097239 A1 | 4/2008 | Chang et al. | |
| 2008/0097295 A1 | 4/2008 | Makower et al. | |
| 2008/0097400 A1 | 4/2008 | Chang et al. | |
| 2008/0097514 A1 | 4/2008 | Chang et al. | |
| 2008/0097515 A1 | 4/2008 | Chang et al. | |
| 2008/0097516 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0125720 A1 | 5/2008 | Kim et al. | |
| 2008/0132938 A1 | 6/2008 | Chang et al. | |
| 2008/0154237 A1 | 6/2008 | Chang et al. | |
| 2008/0154250 A1 | 6/2008 | Makower et al. | |
| 2008/0171991 A1 | 7/2008 | Kourakis | |
| 2008/0172033 A1 | 7/2008 | Keith et al. | |
| 2008/0195041 A1 | 8/2008 | Goldfarb et al. | |
| 2008/0228085 A1 | 9/2008 | Jenkins et al. | |
| 2008/0234720 A1 | 9/2008 | Chang et al. | |
| 2008/0243140 A1 | 10/2008 | Gopferich et al. | |
| 2008/0249500 A1 | 10/2008 | Keith et al. | |
| 2008/0262468 A1 | 10/2008 | Clifford et al. | |
| 2008/0262505 A1 | 10/2008 | Shahoian | |
| 2008/0262508 A1 | 10/2008 | Clifford et al. | |
| 2008/0262509 A1 | 10/2008 | Clifford et al. | |

(56) References Cited

U.S. PATENT DOCUMENTS

| | | |
|---|---|---|
| 2008/0262510 A1 | 10/2008 | Clifford |
| 2008/0275483 A1 | 11/2008 | Makower et al. |
| 2008/0281156 A1 | 11/2008 | Makower et al. |
| 2008/0281300 A1 | 11/2008 | Morriss |
| 2008/0287908 A1 | 11/2008 | Muni et al. |
| 2008/0319424 A1 | 12/2008 | Muni et al. |
| 2009/0005754 A1 | 1/2009 | Soetermans |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0076439 A1 | 3/2009 | Dollar et al. |
| 2009/0076446 A1 | 3/2009 | Dubuclet, IV et al. |
| 2009/0088728 A1 | 4/2009 | Dollar et al. |
| 2009/0093823 A1 | 4/2009 | Chang et al. |
| 2009/0163848 A1 | 6/2009 | Morriss et al. |
| 2009/0163890 A1 | 6/2009 | Clifford et al. |
| 2009/0171336 A1 | 7/2009 | Weber |
| 2009/0187098 A1 | 7/2009 | Makower et al. |
| 2009/0198216 A1 | 8/2009 | Muni et al. |
| 2009/0216196 A1 | 8/2009 | Drontle et al. |
| 2009/0221988 A1 | 9/2009 | Ressemann et al. |
| 2009/0234283 A1 | 9/2009 | Burton et al. |
| 2009/0240112 A1 | 9/2009 | Goldfarb et al. |
| 2009/0240237 A1 | 9/2009 | Goldfarb et al. |
| 2009/0270815 A1 | 10/2009 | Stamp et al. |
| 2009/0299327 A1 | 12/2009 | Tilson et al. |
| 2009/0299374 A1 | 12/2009 | Tilson et al. |
| 2009/0299379 A1 | 12/2009 | Katz et al. |
| 2009/0299401 A1 | 12/2009 | Tilson et al. |
| 2009/0306589 A1 | 12/2009 | Tilson et al. |
| 2009/0312745 A1 | 12/2009 | Goldfarb et al. |
| 2009/0312807 A1 | 12/2009 | Boudreault et al. |
| 2010/0030031 A1 | 2/2010 | Goldfarb et al. |
| 2010/0030113 A1 | 2/2010 | Morriss et al. |
| 2010/0042046 A1 | 2/2010 | Chang et al. |
| 2010/0049166 A1 | 2/2010 | Koenig et al. |
| 2010/0076269 A1 | 3/2010 | Makower et al. |
| 2010/0076437 A1 | 3/2010 | Tilson et al. |
| 2010/0094137 A1 | 4/2010 | Furlong et al. |
| 2010/0099946 A1 | 4/2010 | Jenkins et al. |
| 2010/0100181 A1 | 4/2010 | Makower et al. |
| 2010/0114066 A1 | 5/2010 | Makower et al. |
| 2010/0121308 A1 | 5/2010 | Muni et al. |
| 2010/0152654 A1 | 6/2010 | Tilson et al. |
| 2010/0168511 A1 | 7/2010 | Muni et al. |
| 2010/0174138 A1 | 7/2010 | Chang et al. |
| 2010/0174308 A1 | 7/2010 | Chang et al. |
| 2010/0198135 A1 | 8/2010 | Morriss et al. |
| 2010/0198191 A1 | 8/2010 | Clifford et al. |
| 2010/0198247 A1 | 8/2010 | Chang et al. |
| 2010/0210901 A1 | 8/2010 | Makower et al. |
| 2010/0211007 A1 | 8/2010 | Lesch, Jr. et al. |
| 2010/0217296 A1 | 8/2010 | Morriss et al. |
| 2010/0241152 A1 | 9/2010 | Tilson et al. |
| 2010/0241153 A1 | 9/2010 | Tilson et al. |
| 2010/0241155 A1 | 9/2010 | Chang et al. |
| 2010/0241178 A1 | 9/2010 | Tilson et al. |
| 2010/0256653 A1 | 10/2010 | Kaplan et al. |
| 2010/0268245 A1 | 10/2010 | Chang et al. |
| 2010/0274188 A1 | 10/2010 | Chang et al. |
| 2010/0274222 A1 | 10/2010 | Setliff, III et al. |
| 2010/0298862 A1 | 11/2010 | Chang et al. |
| 2011/0004057 A1 | 1/2011 | Goldfarb et al. |
| 2011/0015612 A1 | 1/2011 | Arcand et al. |
| 2011/0060214 A1 | 3/2011 | Makower |
| 2011/0060276 A1 | 3/2011 | Schaeffer et al. |
| 2011/0071349 A1 | 3/2011 | Drontle et al. |
| 2011/0112512 A1 | 5/2011 | Muni et al. |
| 2011/0160740 A1 | 6/2011 | Makower et al. |
| 2011/0201996 A1 | 8/2011 | Melder |
| 2011/0202037 A1 | 8/2011 | Bolger |
| 2011/0224652 A1 | 9/2011 | Drontle et al. |
| 2011/0288477 A1 | 11/2011 | Ressemann et al. |
| 2011/0295237 A1 | 12/2011 | Eells et al. |
| 2011/0313355 A1 | 12/2011 | Boatman |
| 2011/0313400 A1 | 12/2011 | Boatman |
| 2012/0004616 A1 | 1/2012 | Mitra |
| 2012/0010646 A1 | 1/2012 | Keith et al. |
| 2012/0016298 A1 | 1/2012 | DeLegge et al. |
| 2012/0071824 A1 | 3/2012 | Chang et al. |
| 2012/0116254 A1 | 5/2012 | Morriss |
| 2012/0136207 A1 | 5/2012 | Goldfarb et al. |
| 2012/0172912 A1 | 7/2012 | Ressemann et al. |
| 2012/0184983 A1 | 7/2012 | Chang et al. |
| 2012/0190973 A1 | 7/2012 | Ressemann et al. |
| 2012/0245419 A1 | 9/2012 | Makower et al. |
| 2012/0265094 A1 | 10/2012 | Goldfarb et al. |
| 2012/0283625 A1 | 11/2012 | Keith et al. |
| 2013/0096605 A1 | 4/2013 | Becker |

FOREIGN PATENT DOCUMENTS

| | | |
|---|---|---|
| WO | WO2006020180 | 2/2006 |
| WO | 2006119512 | 11/2006 |
| WO | WO 2006/119512 A2 | 11/2006 |
| WO | 2008036368 | 3/2008 |
| WO | WO 2008/036368 A2 | 3/2008 |
| WO | WO2008045242 | 4/2008 |
| WO | WO2010022108 | 2/2010 |
| WO | 2010025299 | 3/2010 |
| WO | WO2010025299 | 3/2010 |
| WO | WO2011082074 | 7/2011 |
| WO | WO2011084655 | 7/2011 |
| WO | 2012170860 | 12/2012 |

OTHER PUBLICATIONS

International Search Report for International Application No. PCT/US2009/054236, Apr. 16, 2010, p. 1-4.
Written Opinion of the International Searching Authority for International Application No. PCT/US2009/054236, Apr. 16, 2010, p. 1-4.
International Preliminary Report on Patentability for International Application No. PCT/US2009/054236, Feb. 22, 2011.
International Search Report for International Application No. PCT/US2009/055252, Apr. 20, 2010, p. 1-4.
Written Opinion of the International Searching Authority for International Application No. PCT/US2009/055252, Apr. 20, 2010, p. 1-4.
International Preliminary Report on Patentability for International Application No. PCT/US2009/055252, Mar. 1, 2011, p. 1-5.
European Patent Office, EPO Communication for Application No. 09810613.1, Aug. 8, 2012.
International Searching Authority, Invitation to Pay Additional Fees and, Where Applicable, Protest Fee, International Application No. PCT/US2012/041622, Aug. 21, 2012.
European Patent Office, Supplementary European Search Report, Sep. 23, 2011, for European patent application No. 09810613.1.
Panjehpour, Masoud and Bergein F. Overholt, Photodynamic Therapy for Barrett's Esophagus, Interventional and Therapeutic Gastrointestinal Endoscopy (Frontiers of Gastrointestinal Research), 2010, vol. 27, pp. 128-129, S. Karger AG, Basel (Switzerland).
ClearWay OTW Local Therapeutic Infusion Catheter. Product information [online], Atrium [retrieved Nov. 28, 2011]. Retrieved from the internet: URL: http://www.atriummed.com/EN/Interventional/clearway.asp.
ClearWay RX Local Therapeutic Infusion Catheter. Product information [online], Atrium [retrieved Jun. 6, 2011]. Retrieved from the internet: URL: http://www.atriummed.com/EN/cardiology/clearway.asp.
Relieva Stratus MicroFlow Spacers & Relieva Stratus Deployment Guides. Intructions for Use, Acclarent Inc., pp. 1-8.
Relieva Ultirra Sinus Balloon Catheter. Intructions for Use, Acclarent Inc., pp. 1-11.
Flextome Cutting Balloon Dilatation Device. Product Information [online], Boston Scientific [retrieved Feb. 16, 2011]. Retrieved from the internet: URL: http://www.bostonscientific.com/Device.bsci?page=HCP_Overview&navRelId=1000.1003&method=DevDetailHCP&id=10004791&pageDisclaimer=Disclaimer.ProductPage.

(56) References Cited

OTHER PUBLICATIONS

XprESS Multi-Sinus Dilation Tool. Instructions for Use, Entellus Medical, May 2011, pp. 1-6.
XprESS Multi-Sinus Dilation Tool Using Bending Tool. Instructions for Use, Entellus Medical, Sep. 2011, pp. 1-7.

European Patent Office, International Preliminary Report on Patentability, App. No. PCT/US2012/041622, Dec. 27, 2013, pp. 2-11.
European Patent Office, International Search Report and Written Opinion for international application No. PCT/US2012/041622, mailed on Oct. 4, 2012.

* cited by examiner

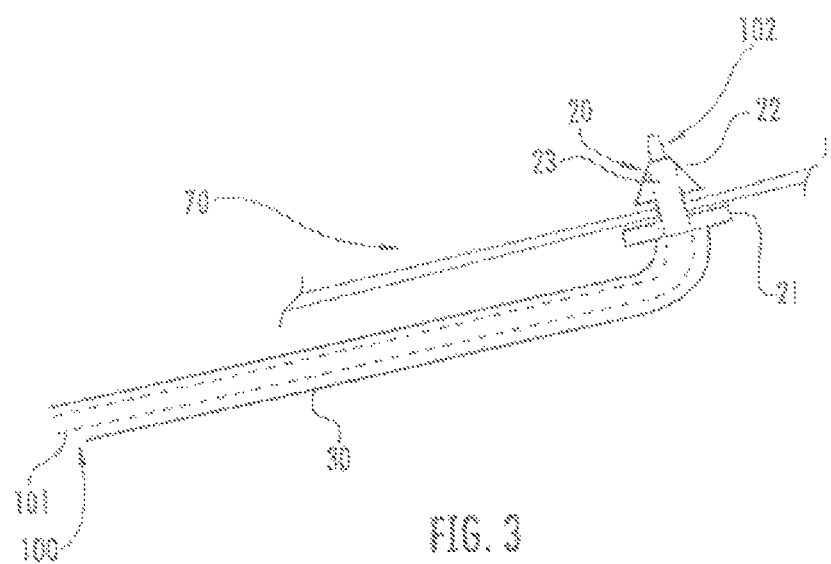

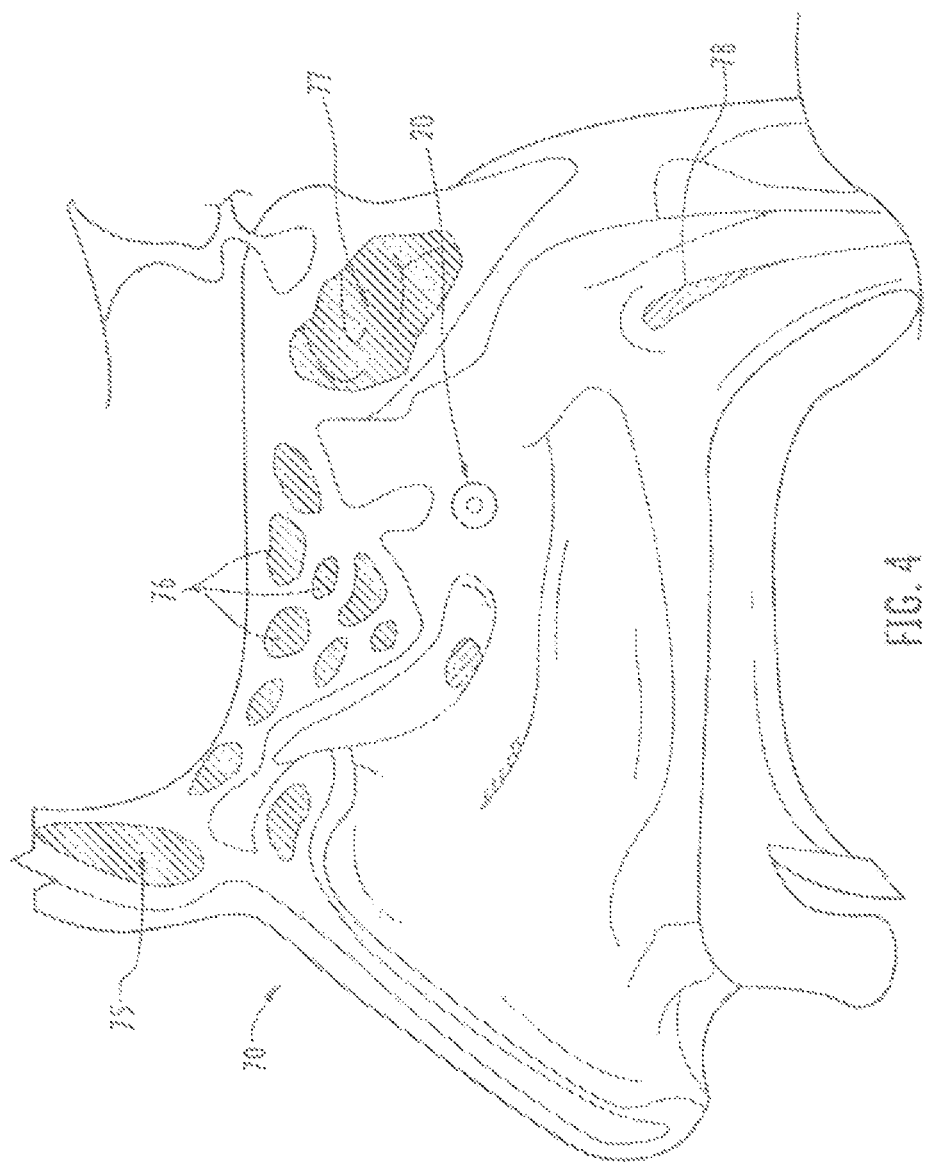

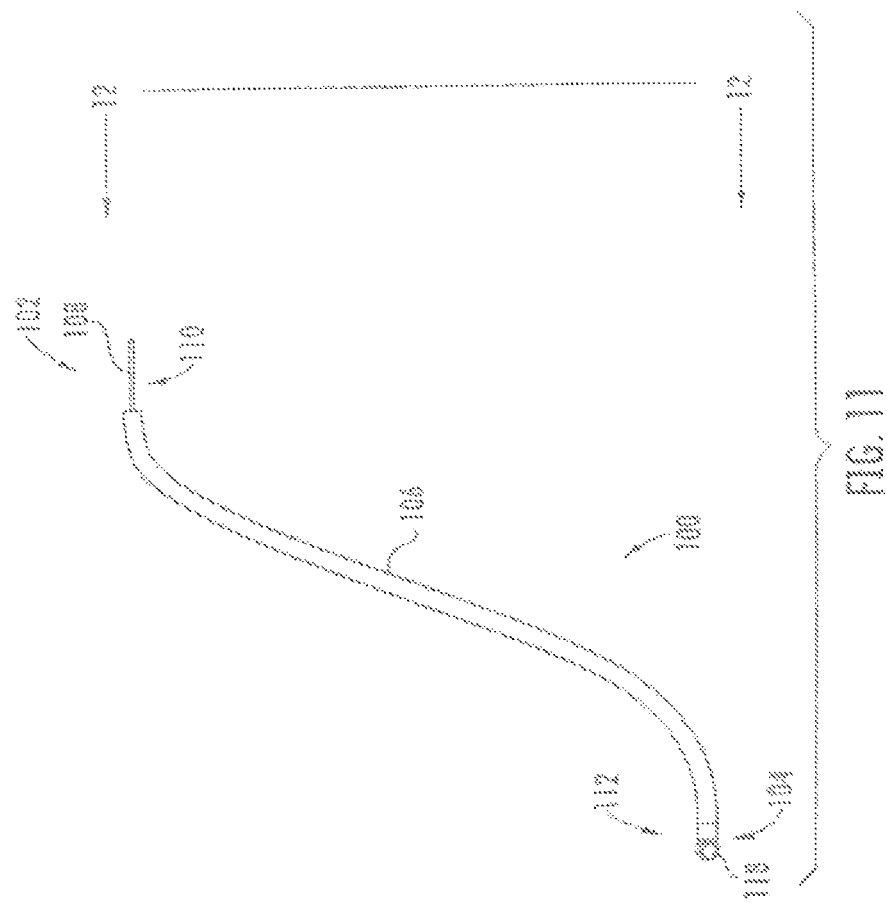
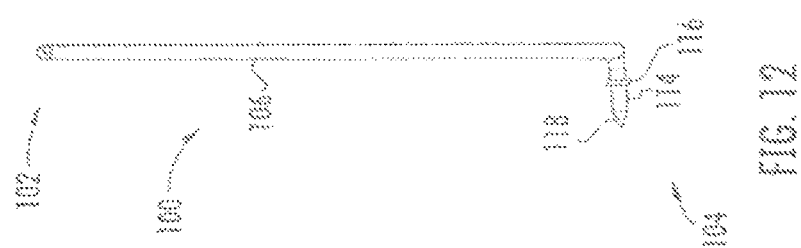

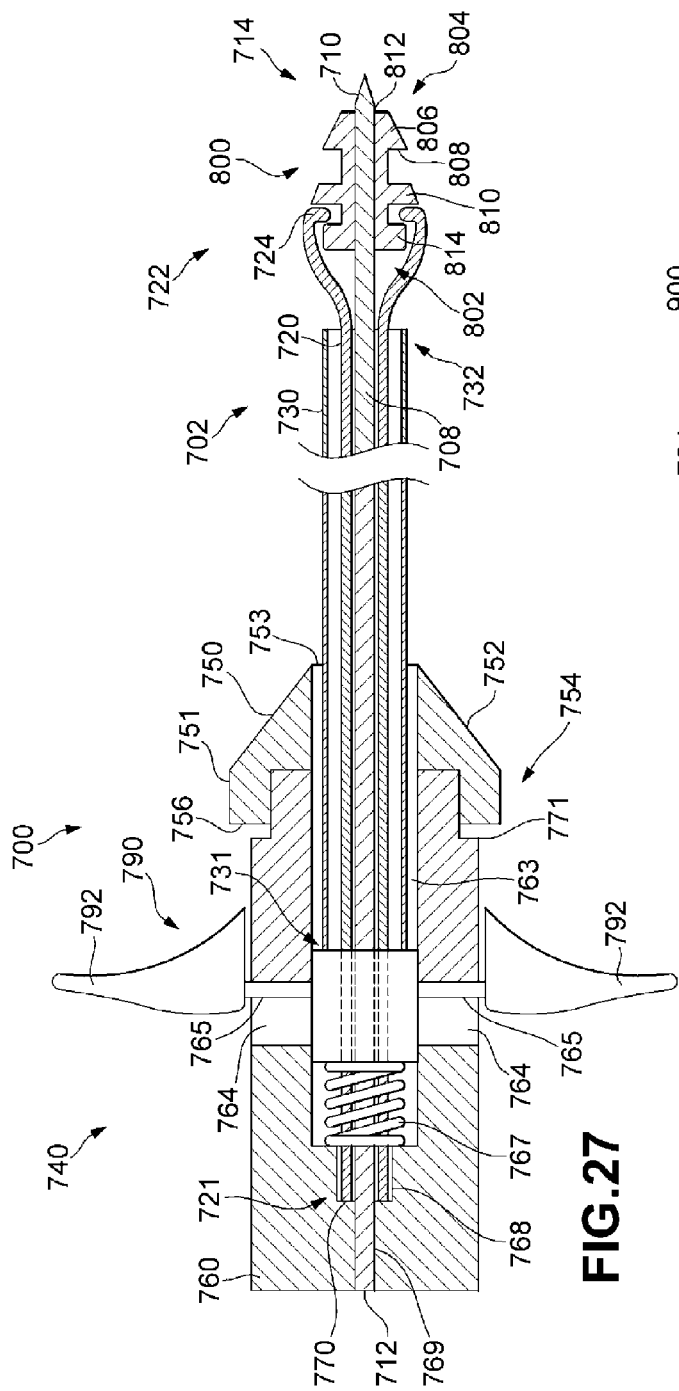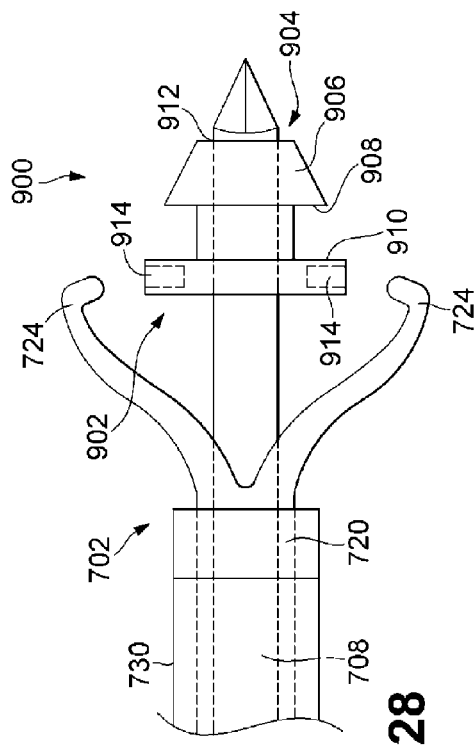
FIG. 27
FIG. 28

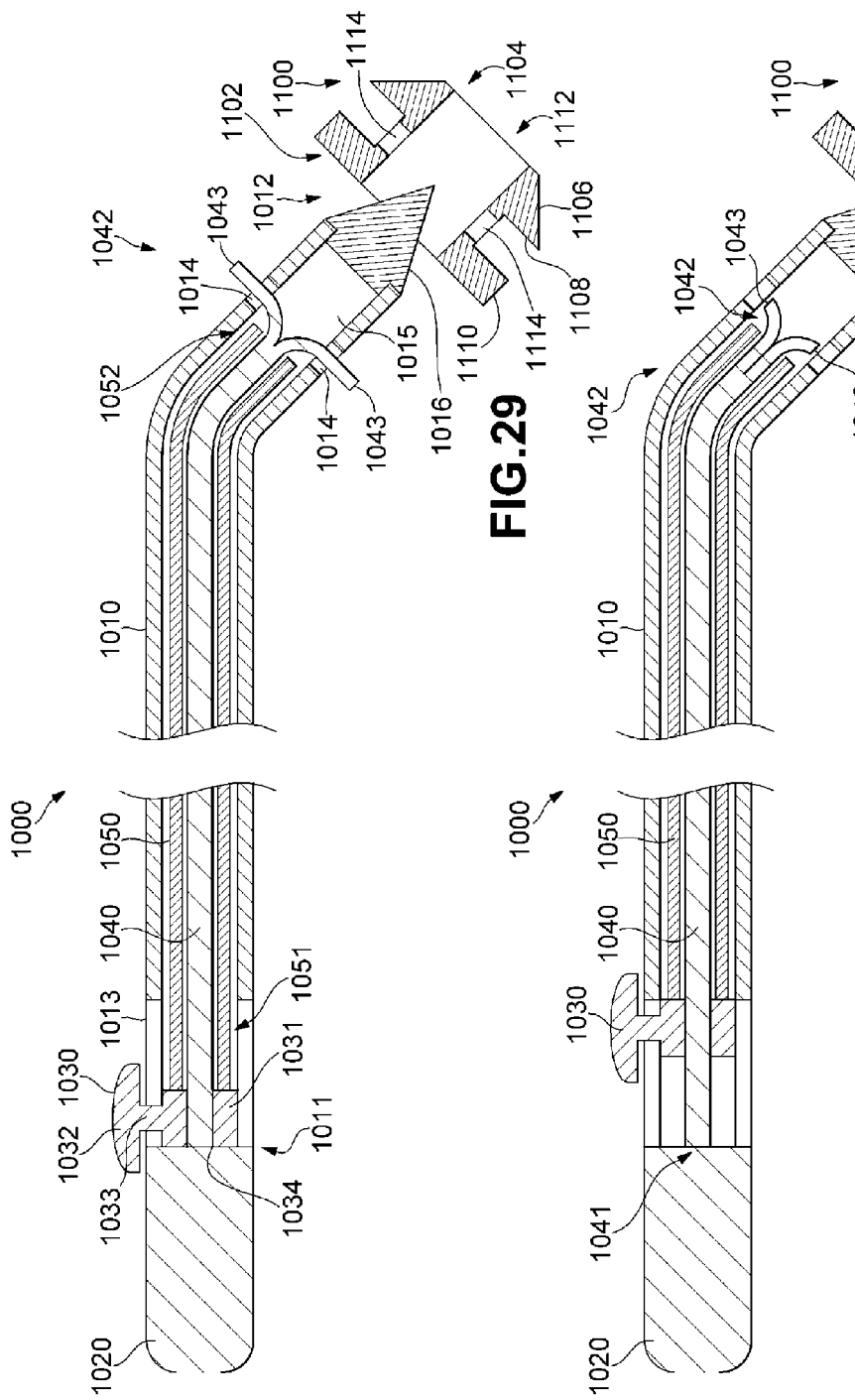

DELIVERY SYSTEM FOR IMPLANTING NASAL VENTILATION TUBE

FIELD

The present invention relates, in general, to functional endoscopic techniques and, more particularly, to apparatuses, systems and methods for ventilating the paranasal sinuses.

BACKGROUND

There has been resurgence of interest among otolaryngologists in the morphological features of the lateral wall of the nasal cavity with the advent of endonasal endoscopic sinus surgery. Functional endoscopic techniques, being minimally traumatic, have become increasingly popular in diagnostic and therapeutic aspects of nasal and sinus problems.

The area termed the "ostiomeatal complex" of the middle meatus has not only the primary maxillary ostia ("PMO") opening in the hiatus semilunaris ("HS") but also often includes, other "holes" or accessory maxillary ostium (AMO). It has been estimated that anywhere between 5-30% of the normal population has an AMO located in the maxillary fontanelle (anterior or posterior).

AMO is invariably solitary but occasionally multiple, either congenital or secondary to disease process. A possible mechanism of formation of accessory ostia is obstruction of the main ostium by maxillary sinusitis or due to anatomic and pathologic factors in the middle meatus resulting in the rupture of membranous areas known as fontanelle (certain regions in the middle meatus located below the uncinate process and above the inferior turbinate, covered by nasal mucous membrane medially and mucosa of maxillary sinus laterally with connective tissue sandwiched between the two).

In the past, a naso-antral window procedure was performed for purposes of ventilation and drainage of the maxillary sinus cavity. However, the naso-antral window procedure has the disadvantage of requiring one or more punctures through thick bony tissues in the inferior meatus.

BRIEF SUMMARY OF THE DISCLOSURE

The medical devices and delivery systems described herein provide for the creation of an AMO for purposes of ventilation, irrigation, drug delivery, or performing procedural work within the maxillary antrum, or other bodily cavity. In particular, delivery systems including an introducer having a ventilation tube are provided to create and then provide access through an AMO. An irrigation, infusion, or balloon catheter may then be advanced through the ventilation tube in order to irrigate, deliver drugs, or express the contents of the sinus cavities. Furthermore, the balloon catheter may be employed to dilate the natural ostium.

Various delivery systems are described, including delivery systems that release a ventilation tube at a point of treatment by a pull operated functionality and delivery systems that release a ventilation tube at a point of treatment by a push operated functionality. Other examples include delivery systems that release a ventilation tube at a point of treatment using one or more grasping elements and/or attachment elements.

Various ventilation tubes are also described, including examples that have varying central channel configurations which assist in attaching the ventilation tubes to a delivery system. Other examples include ventilation tubes that have varying flange and/or aperture configurations to assist in attaching the ventilation tubes to a delivery system.

Various ventilation tube containers are also described, including examples that house one or more ventilation tubes within an elongate structure. Other examples include ventilation tube containers that incorporate a liner to assist with supporting one or more ventilation tubes within the container.

Additional understanding of the systems and devices contemplated and/or claimed by the inventors can be gained by reviewing the detailed description of exemplary embodiments, presented below, and the referenced drawings.

BRIEF DESCRIPTION OF THE DRAWINGS

FIG. 3 of the drawings is an enlarged view of the portion of the antrum showing, in particular, the obturator disposed through the introducer and the ventilation tube.

FIG. 4 of the drawings is an enlarged view of a portion of the lateral nasal wall showing, in particular, the ventilation tube in place after removal of the introducer.

FIG. 11 of the drawings shows a perspective view of another exemplary introducer.

FIG. 12 of the drawings shows a perspective view of the introducer in FIG. 11 taken along lines 12-12 in FIG. 11.

FIG. 27 is a sectional view of another exemplary delivery system and associated ventilation tube.

FIG. 28 is a side view of the distal end of the delivery system illustrated in FIG. 27 and an alternative ventilation tube.

FIG. 29 is a partial sectional view of another exemplary delivery system and associated ventilation tube in the first position.

FIG. 30 is a partial sectional view of the delivery system and ventilation tube illustrated in FIG. 29 in the second position.

DETAILED DESCRIPTION

The following detailed description and the appended drawings are provided to describe and illustrate exemplary embodiments of the invention for the purpose of enabling one of ordinary skill in the relevant art to make and use the invention. The description and drawings are not intended to limit the scope of the invention or its protection in any manner.

Throughout the specification, the terms "proximal" and "distal" are used to describe opposing axial ends of the particular elements or features being described. In addition, the term "device" refers to any device, object, apparatus, or structure, that supports, repairs, or replaces, a part of the body or a function thereof, or is configured to do the same, alone or in combination with other devices or elements.

Figure 1:
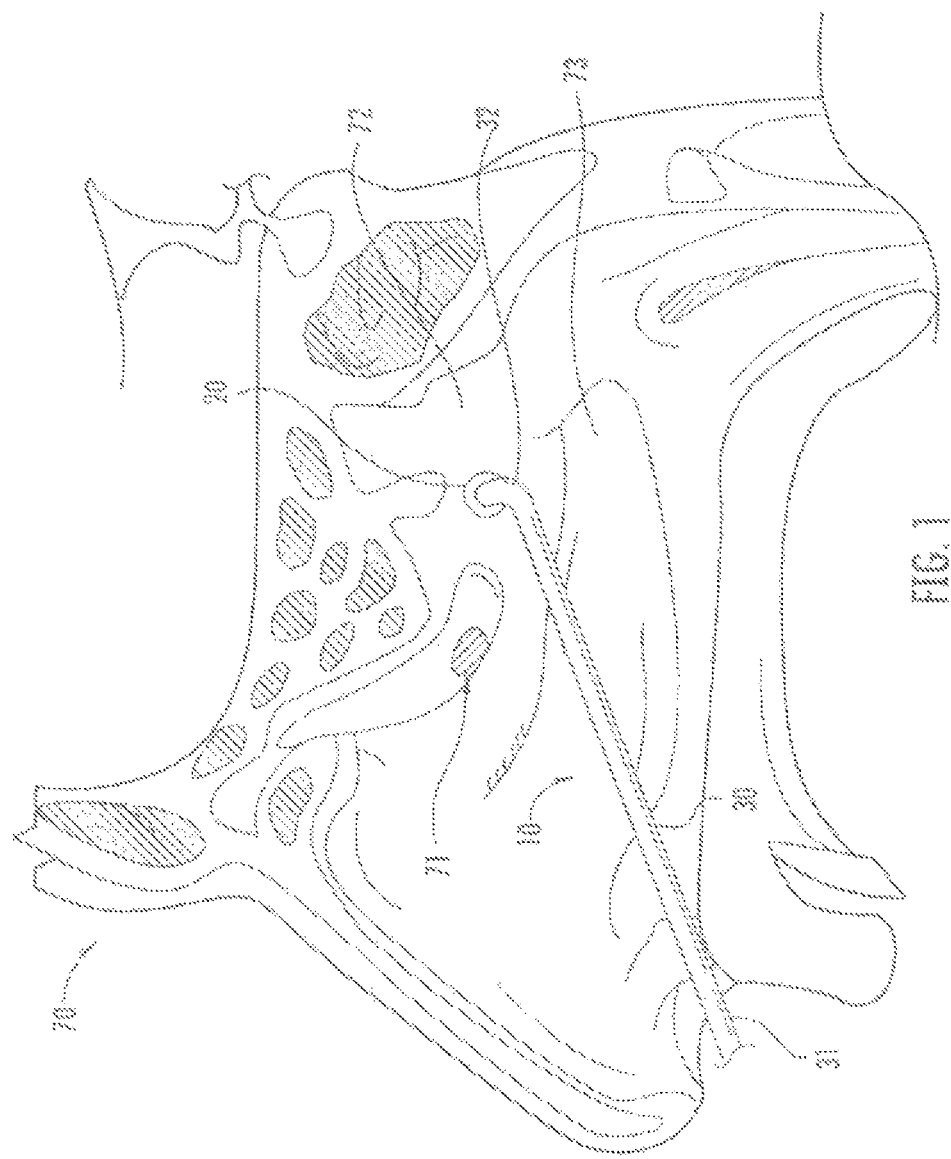
FIG. 1 of the drawings is a sectional view of a human skull showing, in particular, the lateral nasal wall and the orientation of the introducer and ventilation tube.

A nasal ventilation system 10 is shown in FIG. 1 as comprising ventilation tube 20 and elongated introducer 30, suitable for creating an AMO within lateral nasal wall 70 (shown with the middle turbinate and uncinate removed to allow visualization of the natural ostium), proximate maxillary ostium 71, maxillary fontanelle 72, and/or inferior turbinate 73. Furthermore, the nasal ventilation system 10, ventilation tube 20, and elongated introducer 30 are suitable for creating an AMO in other targeted tissues, such as walls of the ethmoid, sphenoid and other paranasal sinuses. A distal tip of introducer 30 is insertable through a central channel of ventilation tube 20, is releasably attachable to ventilation tube 20, and includes a sharp, removable cutting obturator at the distal tip. The cutting obturator can be, however, integrated with, or fixedly attached to, the introducer.

As shown in FIGS. 1 and 3, in operation, introducer 30 with ventilation tube 20 at its distal end are introduced into the middle meatus in the region of the fontanelle (anterior or posterior) under endoscopic assistance, facilitated by the obturator 100. Referring to FIG. 3, obturator 100 includes proximal flexible shaft 101 and sharp distal cutting tip 102. Once the membraneous fontanelle or other targeted area is identified, obturator 100 is advanced through introducer 30 and ventilation tube 20 until cutting tip 102 extends beyond ventilation tube 20, and cutting tip 102 and ventilation tube 20 are pushed through the fontanelle. Obturator 100 and introducer 30 are then removed. An endoscope is preferably employed to provide visualization during this procedure.

Figure 2A:
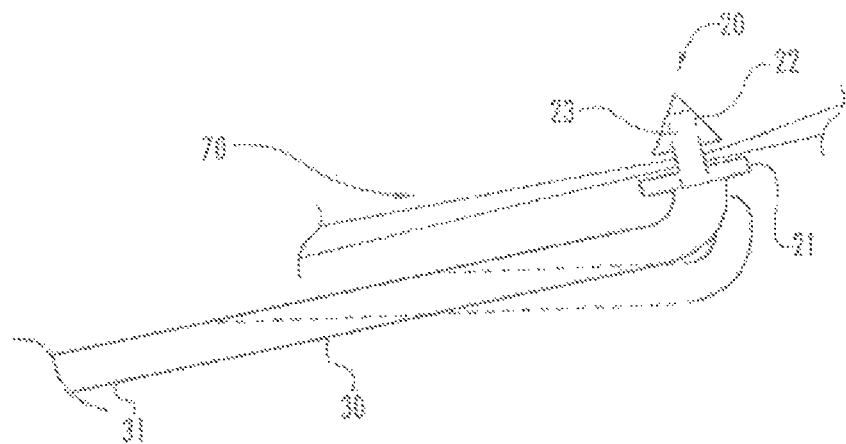
FIG. 2A of the drawings is an enlarged view of a portion of the antrum, or maxillary sinus showing, in particular, the creation of an AMO using the introducer, and the placement of the ventilation tube through the AMO.

Ventilation tube 20 and introducer 30 are shown in further detail in FIG. 2A. Ventilation tube 20 includes grommet-like member or proximal flange 21, retaining member or distal flange 22, and channel 23 extending through ventilation tube 20, terminating in opposing apertures extending through grommet-like member 21, retaining member 22 of ventilation tube 20. As shown in FIG. 2A, upon placement of ventilation tube 20, grommet-like member 21 and conical or frustoconical retaining member 22 are disposed on opposing sides of the AMO extending through lateral nasal wall 70, and serve to maintain ventilation tube 20 in place. As indicated by the phantom lines of FIG. 2A, the introducer 30 can be constructed of a relatively flexible material to permit the introducer 30 to be readily advanced through the paranasal sinus passages to the desired site of the AMO. The introducer 30, or portions thereof, can be, however, constructed of a semi-rigid or rigid material. Skilled artisans will be able to select a particular material for inclusion with an introducer 30 based on various considerations, including the intended use of the ventilation tube, and others.

Ventilation tube 20 may be constructed of a variety of plastic-like materials commonly used in medical devices, including materials commonly employed in middle ear ventilation tubes. Examples of suitable materials include compressible materials, polyetheretherketone, carbothane, nylon, urethane, polyurethane, polyethylene, polyvinylchloride, and other materials. Materials hereinafter discovered and/or developed that are determined to be suitable for use would also be considered acceptable. Moreover, ventilation tube 20 may be constructed of a drug eluting material, and may include compounds such as steroids or minerals/elements to decrease viral contamination, inflammatory reactions, and/or bacterial colonization. Ventilation tube 20 may include other drugs, bioactives, and/or other compounds, such as anti-thrombogenics, antiproliferatives, antibiotics, antivirals, antifungals, anti-inflammatories, anti-biofilm, and/or any other suitable compounds.

Furthermore, ventilation tube 20 may be constructed of a resorbable material, similar to those used in bio-absorbable sutures, and capable of dissolving in situ over time. Examples of suitable resorbable materials include extracellular matrix materials (ECMs), such as small intestine submucosa (SIS), polyglycolic acid, magnesium, chitosan, and other resorbable materials known in the art.

Figure 2B:
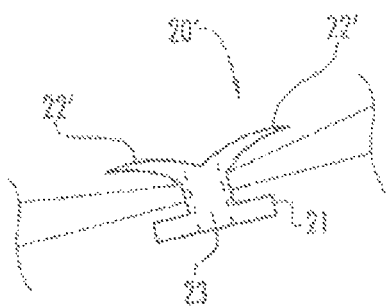
FIG. 2B of the drawings is an enlarged view of the antrum showing, in particular, another exemplary ventilation tube.

An alternative construction of the ventilation tube, namely ventilation tube 20', is shown in FIG. 2B. In this alternative construction, the retaining member comprises expandable feet 22' serving, in cooperation with grommet-like member 21, to retain ventilation tube 20 in place though the membranous fontanelle or other targeted tissue.

Figure 5:
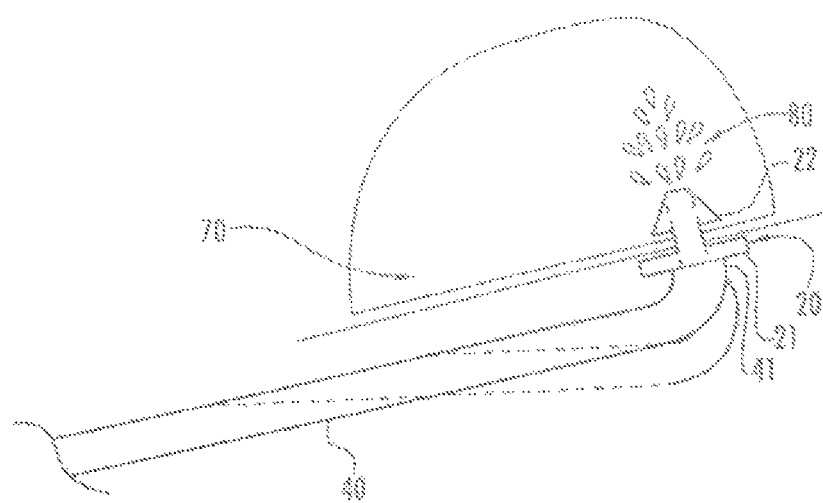
FIG. 5 of the drawings is an enlarged view of a portion of the lateral nasal wall showing, in particular, the use of an irrigation and/or infusion catheter in association with the ventilation tube.

As shown in FIG. 4, once ventilation tube 20 is placed and seated through lateral nasal wall 70 proximate frontal sinus 75, ethmoid sinus 76, sphenoid sinus 78 and Eustachian tube 78, introducer 30 and its associated obturator are separated from ventilation tube 20 and removed. Next, as shown in FIG. 5, irrigation and/or infusion catheter 40 may be placed, by inserting distal tip 41 of catheter 40 into, or entirely through, channel 23 of ventilation tube 20. Irrigation fluid and/or a drug 80 may then be injected into catheter 40 and thus introduced into the desired treatment area to flush the contents of the sinus cavity. The contents of the sinus cavity can then be pushed through the principal or main maxillary ostium to un-block the natural ostium. As indicated by the phantom lines of FIG. 5, irrigation and/or infusion catheter 40 is constructed of a relatively flexible material to permit distal tip 41 of irrigation and/or infusion catheter to be advanced into the paranasal sinuses and placed through ventilation tube 20. The irrigation and/or infusion catheter 40 can be, however, constructed of a semi-rigid or rigid material.

Figure 6:
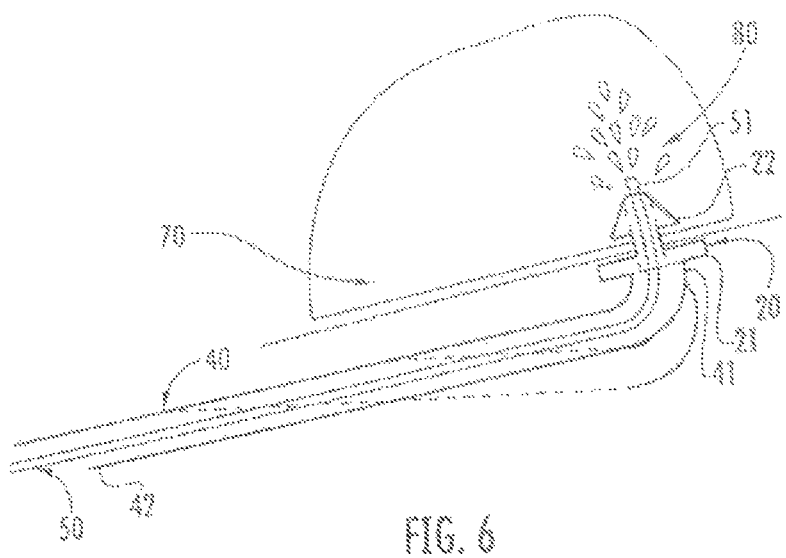
FIG. 6 of the drawings is an enlarged view of a portion of the lateral nasal wall showing, in particular, the use of a second, smaller diameter irrigation and/or infusion catheter within an outer irrigation and/or infusion catheter in association with the ventilation tube.
Figure 7:
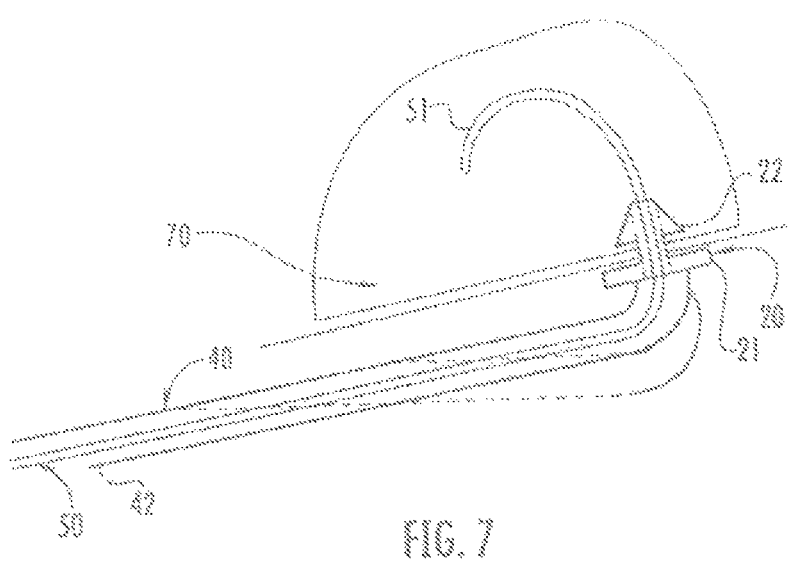
FIG. 7 of the drawings is an enlarged view of a portion of the lateral nasal wall showing, in particular, the second irrigation and/or infusion catheter extended deeply into the sinus cavity.

As shown in FIG. 6, a separate, smaller diameter secondary irrigation and/or infusion catheter 50 may be used in conjunction with irrigation and/or infusion catheter 40. Distal tip 51 of secondary catheter 50 is inserted through an opening at proximal end 42 of catheter 40, and is advanced beyond distal tip 41 of catheter 40 and into the targeted sinus cavity. Irrigation fluid and/or a drug 80 is then injected into the secondary catheter 50 and is thus introduced to the desired treatment area to flush the contents of the sinus cavity. Moreover, and as shown in FIG. 7, distal tip 51 of secondary catheter 50 may be inserted more deeply into the targeted sinus cavity to deeply instill liquids within the antrum, by further advancing secondary catheter 50 through catheter 40.

Figure 8:
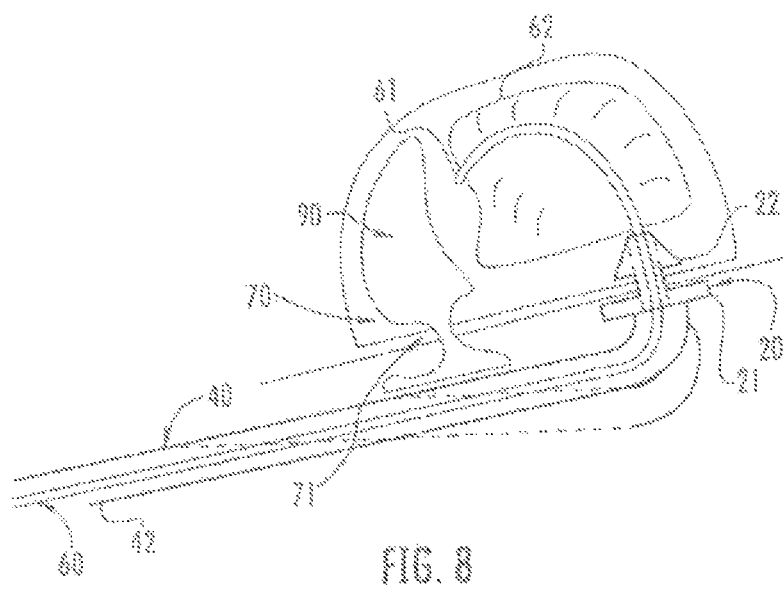
FIG. 8 of the drawings is an enlarged view of a portion of the lateral nasal wall showing, in particular, the use of a balloon catheter within the sinus cavity.

Alternatively, and as shown in FIG. 8, balloon catheter 60 may be employed in place of secondary irrigation catheter 50. Balloon catheter 60 includes distal tip 61, and expansile member 62 surrounding a distal portion of the main lumen of the balloon catheter 60. As shown in FIG. 8, distal tip 61 may be placed through irrigation and/or infusion catheter 40 and advanced deeply into the targeted sinus cavity. Expansile member 62 is then inflated. This, in turn, causes the contents of the sinus cavity, such as mucous or purulent debris 90, to be expressed through the natural PMO 71.

Figure 9:
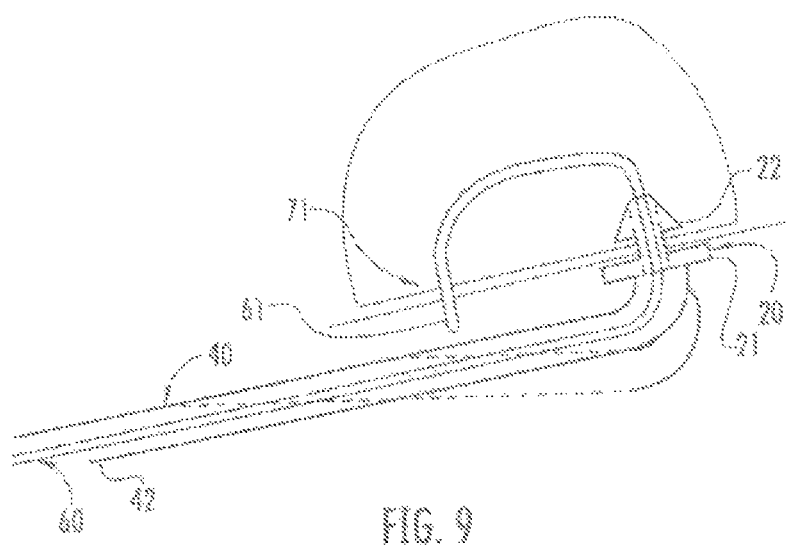
FIG. 9 of the drawings is an enlarged view of a portion of the lateral nasal wall showing, in particular, the placement of a balloon catheter within the natural ostium.
Figure 10:
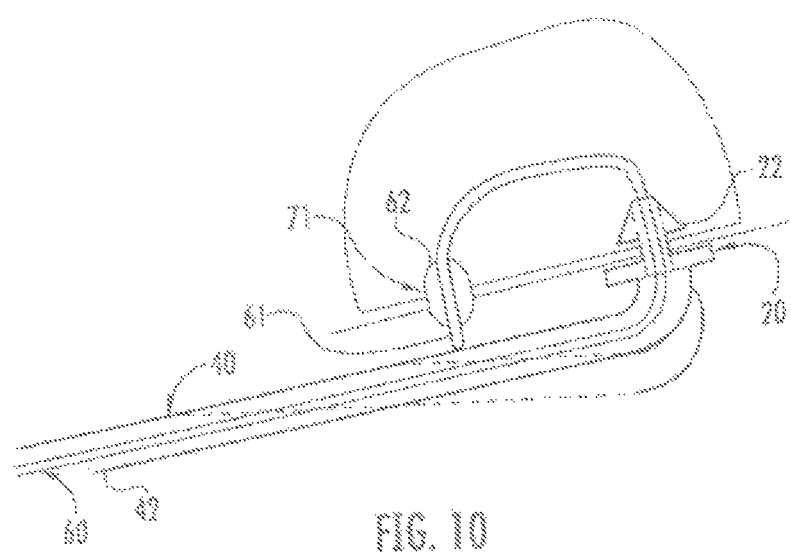
FIG. 10 of the drawings is an enlarged view of a portion of the lateral nasal wall showing, in particular, the expansion of the balloon catheter for dilation of the natural ostium.

As shown in FIG. 9, distal tip 61 of balloon catheter 60 may alternative or additionally be advanced through irrigation and/or infusion catheter 40 and the sinus cavity to extend through the natural PMO 71. Next, as shown in FIG. 10, expansile member 62 is inflated, in order to dilate the natural PMO 71.

Various methods of treating a sinus cavity are described herein. An initial step comprises inserting a ventilation tube at a point of treatment (e.g., within an AMO or other opening in a wall of a sinus cavity, such the paranasal sinus cavities). Another step comprises advancing the distal end of a catheter (e.g., a irrigation, infusion, and/or balloon catheter) through the channel of the ventilation tube such that the distal end of the catheter is in the targeted sinus cavity. Alternatively, the distal end of the catheter is advanced partially into the channel such that the distal end of the catheter is positioned within the channel of the ventilation tube. Another step comprises introducing an irrigation fluid or drug into the targeted sinus cavity. This step can be accomplished by passing the fluid or drug through the catheter while the distal end of the catheter is disposed in the targeted sinus cavity or in the channel of the ventilation tube. Alternatively, this step can be accomplished by passing another catheter through the previously placed catheter, connecting another catheter to the previously placed catheter, or other similar approach. Another step comprises withdrawing the catheter from the channel of the ventilation tube. Another step comprises removing the ventilation tube from the point of treatment, if desired.

Additional, and/or alternative, steps can be included within the above described method. For example, the step of introducing an irrigation fluid or drug into the targeted sinus cavity can alternatively comprise inflating a balloon on the catheter. This step can be accomplished by passing a material through the catheter to inflate the balloon while the distal end of the catheter is disposed in the targeted sinus cavity. Alternatively, this step can be accomplished by passing another catheter through the previously placed catheter and past the distal end of the previously placed catheter.

In an additional example, the step of advancing the distal end of a catheter through the channel of the ventilation tube such that the distal end of the catheter is in the targeted sinus cavity can alternatively comprise advancing the distal end of the catheter through a natural PMO. Alternatively, this step can be accomplished by passing another catheter through the previously placed catheter and past the distal end of the previously placed catheter. Another step comprises inflating a balloon on the catheter. This step can be accomplished by passing a material through the catheter to inflate the balloon while the distal end of the catheter is disposed within the PMO.

Any ventilation tube, including the ventilation tubes described herein, can be used to assist in performing the above-described method. For example, the method can comprise the use of a ventilation tube as described above, and/or below, and illustrated in FIGS. 2A, 2B, 13A, 13B, 25, 26, 27, 28, 29, 30, or any alternatives thereof. Alternatively, the method can comprise the use of a catheter as described below and illustrated in FIG. 14.

FIG. 11 is a perspective view of another exemplary elongated introducer 100. The introducer 100 includes a proximal end 102 and a distal end 104. A tube or shaft 106 extends between the proximal end 102 and distal end 104. A rod 108 extends within the tube 106. The rod 108 includes a proximal end 110 extending out of tube 106 and a distal end (not shown) located at the distal end 104 of the introducer 100. An obturator 112 is located at the distal end 104. In one configuration, the obturator 112 is secured to the distal end of the rod 108. FIG. 12 is a view of the elongated introducer 100 taken along line 12-12 in FIG. 11. FIG. 12 shows the obturator 112 includes a shaft 114, a flange 116 and a sharp, distal cutting tip 118. The shaft 114 may be cylindrical or conical shaped, for example. The elongated introducer 100 may be coupled to a myringotomy apparatus or handle. Such an apparatus typically includes a mechanism to secure the tube 106 in a stationary manner with respect to the apparatus. The rod 108 may be coupled to a trigger mechanism for slidingly activating and controlling the rod 108 with respect to the tube 106. Thus, activation of the trigger of the apparatus controls movement of the obturator 112. The tube 106 of the introducer 100 may be made of a flexible or malleable material to permit the introducer 100 to be readily advanced through the paranasal sinus passages to the desired site of the AMO. The tube 106 can be, however, made of a semi-rigid or rigid material, and skilled artisans will be able to select an appropriate material according to a particular embodiment based on various considerations, include the intended use of the ventilation tube, and the intended use of the introducer.

Figure 13A:
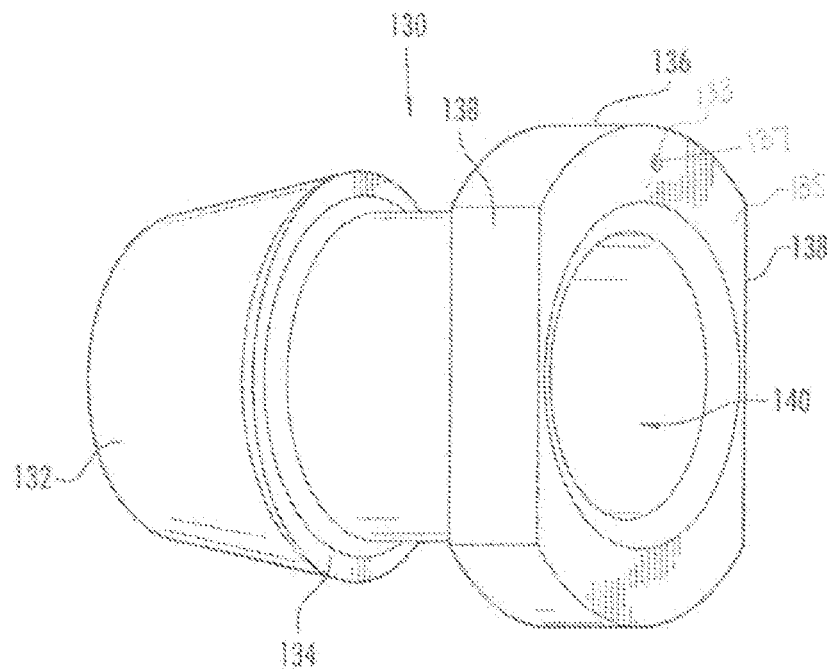
FIG. 13A is a perspective view of an exemplary ventilation tube.

FIG. 13A shows another ventilation tube 130. The ventilation tube 130 includes the conical or frusto-conical retaining member 132, a shoulder 134, grommet-like member 136 having flat side edges 138, and a wall that defines a central channel or bore 140 extending through the ventilation tube 130 from the proximal end of the ventilation tube 130 to the distal end of the ventilation tube 130.

The grommet-like member 136 defines an opening 133 that extends through the grommet-like member 136 from a proximal surface 135 to an opposing distal surface (not illustrated in Figure). Alternatively, the opening 133 defined by the grommet-like member 136 extends from the proximal surface 135 to a side surface of the grommet-like member 136. As such, opening 133 provides access to a through passageway 137 that extends through a thickness of grommet-like member 136.

Opening 133 provides structure useful in retrieval of ventilation tube 130 prior to, during, or following placement through the lateral nasal wall. To use opening 133 for this purpose, a user can pass an elongate member (e.g., thread, suture, or other suitable element) (not illustrated in Figure) through the passageway 137 prior to delivering the ventilation tube 130 to a point of treatment. Both ends of the elongate member can be left free of the ventilation tube, or one end can be free and the other end fixed to the ventilation tube 130. When retrieval of the ventilation tube 130 is desired, the user can simply pull on one or both ends of the elongate member, as appropriate, to pull the ventilation tube 130 from the lateral nasal wall. If retrieval is not necessary, or desired, following placement of the ventilation tube 130, the elongate member can simply be removed from the passageway 137 as appropriate (e.g., by pulling on one free end and allowing the other free end to pass through the passageway 137).

As understood from the above description, the obturator 112 receives the ventilation tube 130. In particular, the shaft 114 is designed to be received by the central channel 140. The shaft 114 and channel 140 may be designed to provide a releasable locking engagement, such as an interference press fit or a snap-fit engagement. The shaft 114 may be cylindrical or conical, for example, with the central channel 140 similarly shaped for a mating engagement. With the obturator 112 inserted into the ventilation tube 130, the flange 116 and grommet-like member 136 limit the depth in which the obturator 11 is inserted within the central channel 140. With the flange 116 engaging the grommet-like member 136, the sharp distal cutting tip 118 projects beyond the conical retaining member 132. Thus, the combined introducer 100 and ventilation tube 130 are adaptable for piercing the tissue and forcing the ventilation tube 130 in place, with the shoulder 134 on one side of the wall and the grommet-like member 136 on the other side of the wall.

Figure 13B:
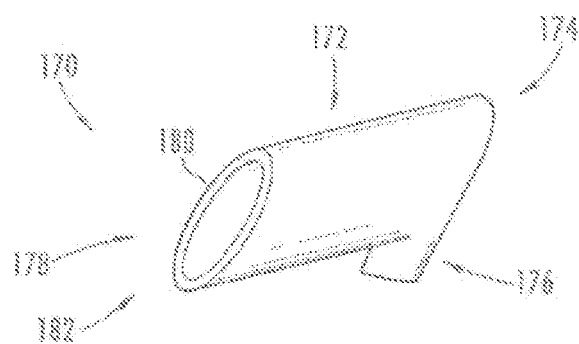
FIG. 13B is a perspective view of another exemplary ventilation tube.

The ventilation tube may take other forms such as omitting the distal flange. In FIG. 13B, another exemplary ventilation tube is shown. In particular, ventilation tube 170 shows a neck portion or sleeve 172 having a proximal end 174 with a proximal flange 176. As an example, the flange may be tab shaped as shown in FIG. 13B or annular shaped. The distal end 178 includes a beveled edge 180 which provides a sharp cutting tip 182. The ventilation tube 170 shown in FIG. 13B is more readily inserted by use of forceps (not shown). For example, the forceps may grip the proximal flange or tab 176. The forceps will be used to guide the tube in place, urging the sharp cutting tip 182 through the sinus wall, and wherein the tab will also limit the insertion depth of the ventilation tube. It will be appreciated that an obturator is not required for inserting the tube 170 into the wall.

In addition, it will be appreciated that the forceps may be used instead of the introducer described above. However, when the term "introducer" is used herein, it is intended to include forceps.

Figure 14:
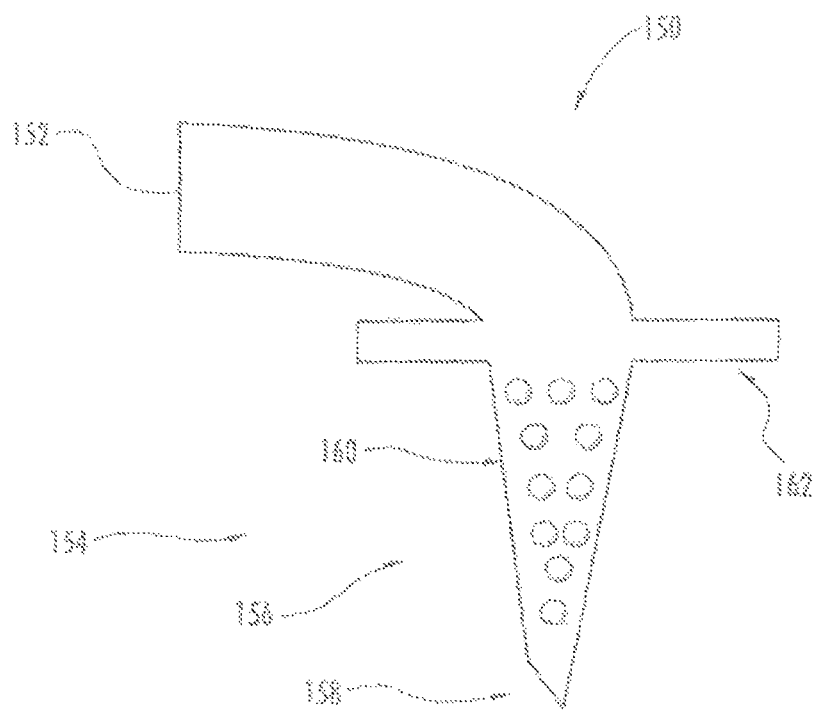
FIG. 14 is another exemplary catheter for delivering drugs and pharmaceuticals.

FIG. 14 shows another exemplary catheter used for delivering a pharmaceutical drug, fluid or the like to the sinus cavity. The catheter 150 is a graphical representation. The catheter 150 includes a hollow shaft 152. The shaft 152 may be of a malleable material or flexible material to permit the catheter to be readily advanced through the sinus passages for creation of an AMO through a wall of the sinus passage or a sinus cavity by pressing the distal end 154 through the wall or other targeted area. Also, the distal end 154 can be advanced through an existing AMO, such as an AMO within which a ventilation tube has been implanted, as described herein. It will be appreciated that the shaft 152 will be proportionally longer than that shown in FIG. 14. The distal end 154 of the catheter 150 includes an irrigation tip 156. The irrigation tip 156 may be generally conical in shape. The conical shape more readily accommodates insertion of the tip 156 into the ventilation tube 130. The irrigation tip 156 may be hollow to provide for fluid and drug flow from the shaft. The irrigation tip 156 may include a delivery opening 158 at the distal end 154. In addition, the wall of the irrigation tip 156 may include micro pore perforations 160. The delivery openings 158 and micro pore perforations 160 provide delivery of the drug or fluid. A flange 162 is provided to limit the insertion depth of the catheter 150. The flange 162 will engage the grommet-like member to limit the insertion of the catheter.

It will be appreciated that the ventilation tube may be used to deliver topical fluids, drugs, anti-inflammatory medications, such as steroids, gene treatments, drug delivery substances, drug impregnated coils, beads, and others through simple insertion or via powered pulsation. For example, a device for delivering such items, such as the catheter 150 for example, may be guided toward the inserted ventilation tube, whereupon the desired item may be delivered directly to the sinus, or in a manner consistent with the description herein. In addition, the delivery device may be adapted for insertion into the first catheter, to assist in guiding the delivery device to the ventilation tube.

Figure 15:
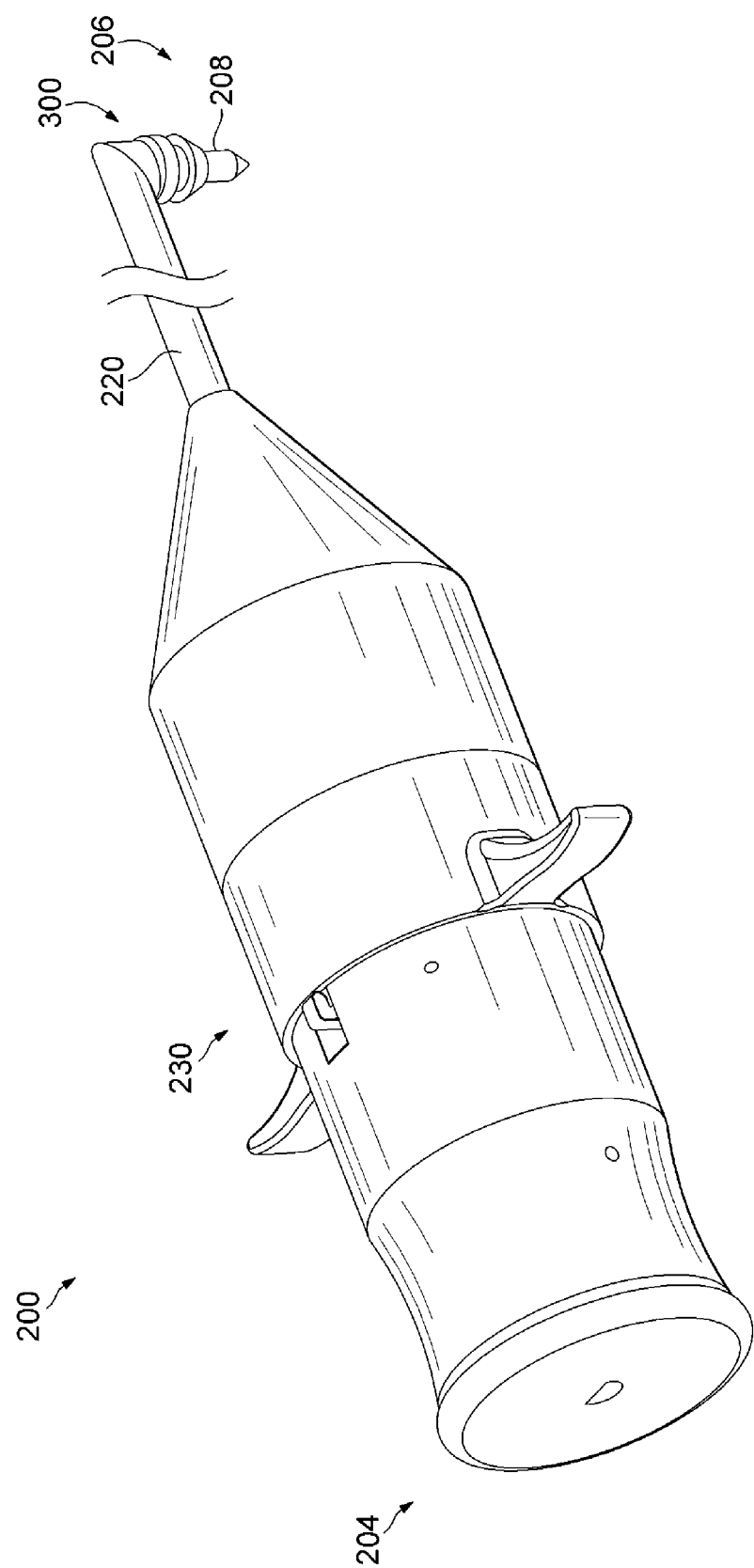
FIG. 15 is a perspective view of an exemplary delivery system and an associated ventilation tube.
Figure 16:
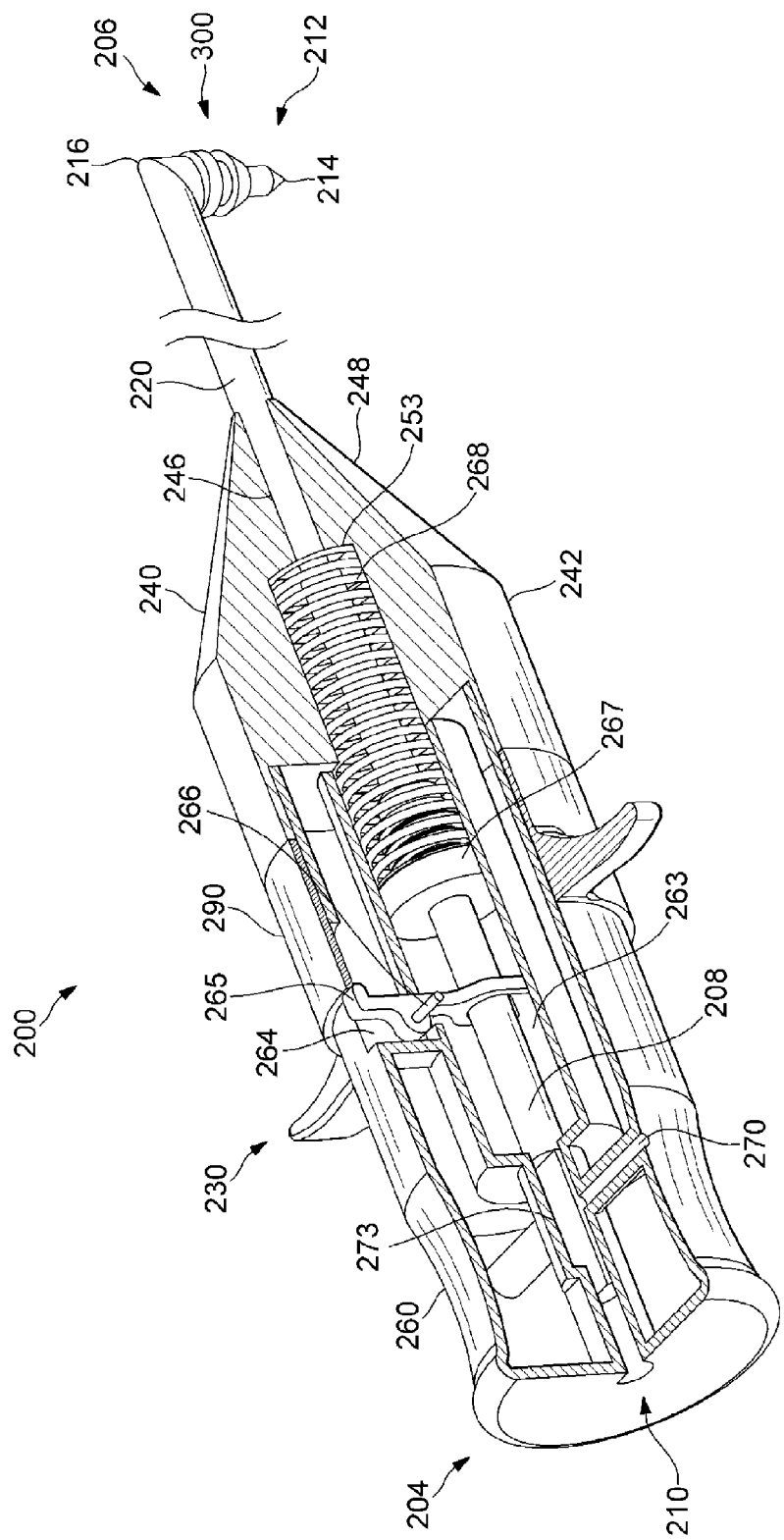
FIG. 16 is a partial sectional view of the delivery system and associated ventilation tube illustrated in FIG. 15.
Figure 17:
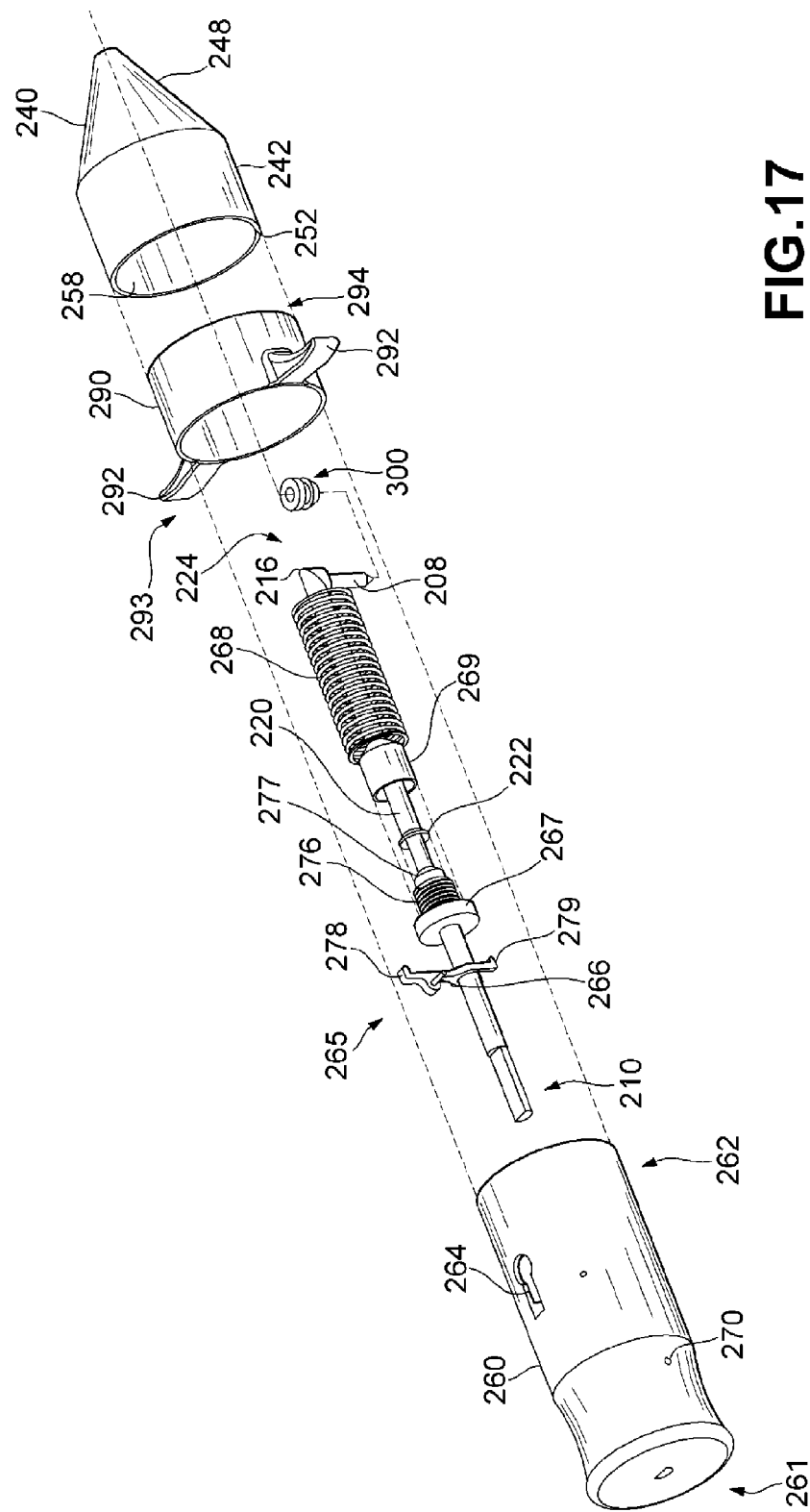
FIG. 17 is an exploded view of the delivery system and associated ventilation tube illustrated in FIG. 15.

Delivery systems for creating an AMO and implanting a ventilation tube are described below. An exemplary delivery system 200 and associated ventilation tube 300 are illustrated in FIGS. 15 through 17. The delivery system 200 comprises a proximal end 204, a distal end 206, an introducer 208, a cannula 220, and a handle 230. The ventilation tube 300 is similar to that described above with respect to FIG. 13A and is disposed on the distal end 206 of the delivery system 200. While the illustrated delivery system 200 includes a ventilation tube 300 similar to that illustrated in FIG. 13A, any suitable ventilation tube can be used in combination with the delivery system 200, and skilled artisans will be able to select an appropriate ventilation tube for inclusion with a delivery system according to a particular embodiment based on various considerations, including the intended use of the delivery system, the intended use of the ventilation tube, and others.

The introducer 208 comprises an elongate rigid structure having a lengthwise axis, a proximal end 210, distal end 212, sharp distal tip 214, and a bend 216. The proximal end 210 of the introducer 208 has a semi-circular configuration, or any other suitable configuration, and the distal end 212 of the introducer 208 includes a region between the sharp distal tip 214 and bend 216 for receiving the ventilation tube 300. As described below, various configurations of the distal end 212 of the introducer 208 can be used to releasably attach the ventilation tube 300 to the introducer 208. While the introducer 208 has been described as rigid in nature, a semi-rigid, malleable, flexible, or tubular introducer can be used in combination with the delivery system 200, and skilled artisans will be able to select a suitable material and structure for an introducer for inclusion with a delivery system according to a particular embodiment based on various considerations, including the intended use of the delivery system, and the intended use of the introducer.

The ventilation tube 300 is releasably disposed on the distal end 212 of the introducer 208 and has a wall which defines a channel extending between the proximal end and the distal end of the ventilation tube 300. The channel has a resting diameter and a loaded diameter, which is described in more detail below.

The cannula 220 is slidably disposed over the introducer 208 and comprises a flexible tubular structure having a flared proximal end 222, a distal end 224, and an outside diameter. The flared proximal end 222 is disposed within the handle. The distal end 224 of the cannula 220 is disposed proximal to the distal end 212 of the introducer 208, leaving a portion of the introducer 208 exposed to receive the ventilation tube 300. The distal end 224 of the cannula 220 is angled to provide a surface to interact with the proximal end of the ventilation tube 300. For example, the distal end 224 of the cannula 220 can define an angle which is in a plane that is substantially parallel to a plane containing the proximal surface of the ventilation tube 300. The distal end 224 of the cannula 220 can be, however, straight or otherwise angled. The cannula 220 has a thickness which allows the distal end 224 to interact with the proximal end of the ventilation tube 300 and wrap around bend 216. While the cannula 220 has been described as flexible in nature and having a flared proximal end 222, a semi-rigid, malleable, or rigid cannula can be used in combination with the delivery system 200, and the flared proximal end 222 can be omitted, and skilled artisans will be able to select a cannula for inclusion with a delivery system according to a particular embodiment based on various considerations, including the intended use of the delivery system, the intended use of the cannula, and others.

The length, number of bends, and the angle of the bends defined by the introducer 208 and/or cannula 220 can vary depending on the application, and skilled artisans will be able to select a suitable length, number of bends, and angle based on various considerations, such as the environment in which the delivery system is intended to be used, the type of procedure being performed, and the configuration of the distal end of the delivery system. Examples of suitable numbers of bends include one, two, three, four and any other number determined suitable for a particular application. Examples of angles considered suitable for the bend include angles in the range from about 0° to about 180°. Exemplary angles considered suitable for the bend include angles in the range from about 20° to about 160°. Further exemplary angles for the bend include angles in the range from about 45° to about 135°.

One or both of the introducer 208 and the cannula 220 can be formed of a malleable material adapted to allow a user to bend and/or shape the introducer 208 and/or cannula 220 before or during a procedure in which the delivery system is used 200 to access a bodily passage of a patient. For example, a delivery system having one or both of the introducer and cannula formed of a malleable material can allow a user to bend and/or shape one or both components to conform to actual or expected patient anatomy, such as a sinus passage, a bodily passage that provides access to a sinus passage, or any other bodily passage. The introducer 208 and/or cannula 220 can comprise segments which vary in stiffness and flexibility. For example, flexible segments can correspond to bend 216 in the introducer 208 and/or cannula 220, while more rigid segments could correspond to straight portions of the introducer 208 and/or cannula 220. Example materials considered suitable for the introducer 208 and/or cannula 220 include 304SS, NiTi, polymeric materials, or metallic laser cut flexing components. Braided and/or coiled polymeric materials are also considered suitable. Skilled artisans will be able to select suitable materials for the introducer and/or cannula according to a particular embodiment based on various considerations, including the intended use of the delivery system, the intended use of the introducer and/or cannula, and others.

In these embodiments, it is considered advantageous to provide a cap disposed on the distal end 212 of the introducer 208 covering the sharp distal tip 214. If included, the cap can comprise any suitable structure capable of being releasably attached to the sharp distal tip 214 and of covering the sharp distal tip 214. The cap can be formed of any suitable material, including plastic and metal materials. In one embodiment, the cap is a cup-shaped member that defines a receptacle sized and configured for receiving the sharp distal tip 214. The cap has an inner diameter slightly smaller than the outer diameter of the distal end 212 of the introducer 208 when the cap is free of the introducer 208. This configuration advantageously provides a friction fit between the distal end 212 of the introducer 208 and the cap when the cap is disposed on the distal end 212 of the introducer 208. Inclusion of the cap is considered advantageous at least because it can cover the sharp distal tip 214 during an initial placement of the introducer 208 into a bodily passage, such as during a preliminary shaping procedure in which a user conforms the shape and/or configuration of the introducer 208 and/or cannula 220 to the anatomy of a particular patient. When using a delivery system according to these embodiments, a user initially inserts the distal end 212 of the introducer 208, with the cap disposed thereon and covering the sharp distal tip 214, into a bodily passage, such as a sinus passage or a bodily passage that provides access to a sinus passage, and manipulates the introducer 208 and/or cannula 220 to conform to the anatomy of the bodily passage. During this process, the cap provides a barrier between the sharp distal tip 214 and the tissue lining the bodily passage. Once a desired shape and/or configuration is achieved, the user can then remove the cap to expose the sharp distal tip 214 and continue with the procedure (e.g., loading a ventilation tube).

The handle 230 is disposed on the proximal end 210 of the introducer 208 and comprises a head member 240, a housing 260, and a finger retraction handle 290. The head member 240 is disposed on a distal end of the housing 260, defines a lumen 246 extending through the length of the head member 240, and has a tapered distal end 248, an annular proximal end 242, and a proximal edge 252. The lumen 246 of the head member 240 has a varying diameter and includes an interior surface 253 defined by the stepped configuration of the lumen 246. The tapered distal end 248 extends proximally and away from the center of the lumen 246 to the annular proximal end 242 which extends proximally to proximal edge 252. The annular proximal end 242 of the head member 240 has an inner diameter 258 and depth sufficient to receive a portion of the distal end 262 of the housing 260.

The housing 260 has a varying outer diameter and comprises a proximal end 261, a distal end 262, a cavity 263, an elongate aperture 264, a rocker arm 265, a pin 266, a drum 267, a spring 268, a cap 269, and channels 270. The distal end 262 of the housing 260 has an outer diameter and length sufficient to be received by, and attached to, a portion of the head member 240. The elongate aperture 264 extends through the housing 260 and provides access to the cavity 263. The cavity 263 is in communication with the lumen 246 of the head member 240 and contains the drum 267 and spring 268. The housing 260 can be attached to the head member 240 using various methods, and skilled artisans will be able to select an appropriate method according to a particular embodiment based on various considerations, including the intended use of the delivery system, and the intended use of the ventilation tube. Example methods of attaching the head member 240 and the housing 260 include snap fitting, adhesively affixing, using a set screw and/or pin, and any other method considered suitable for a particular application.

The cavity 263 extends through the length of the housing 260 and defines a lumen 273 at the proximal end of the cavity 263 having a diameter less than the cavity 263. The channels 270 extend through the housing 260 and provide access to the lumen 273 which has a proximal end with a semi-circular configuration. The introducer 208 extends through the drum 267 and spring 268 and through the cavity 263 and lumen 273. The proximal end 210 of the introducer 208 has a configuration that mirrors the semi-circular configuration of the proximal end of the lumen 273 which reduces and/or eliminates rotation of the introducer 208 when the delivery system 200 is in use. The proximal end 210 of the introducer 208 can be adhesively affixed within the lumen 273 using channels 270 to apply an adhesive material. Alternatively, the proximal end 210 of the introducer 208 can be releasably affixed, or integrated with, the housing 260.

While the introducer 208 has been described as being adhesively affixed to the housing 260, other methods of attaching the introducer to the housing can be used, and skilled artisans will be able to select an appropriate method of attachment according to a particular embodiment based on various considerations, including the intended use of the delivery system, and the intended use of the ventilation tube. Example methods of attaching the introducer 208 to the housing 260 include insert molding, using a set screw and/or pin, and any other method considered suitable for a particular application. For example, the structure of the introducer 208 can be altered, such as by roughening the proximal end 210 of the introducer 208, to facilitate attachment to the housing 260 by applying an adhesive or insert molding.

The drum 267 has a threaded distal end 276 that includes a taper 277 that mirrors the flared proximal end 222 of the cannula 220. The drum 267 is attached to the flared proximal end 222 of the cannula 220 by sliding cap 269, which has a threaded inner diameter, over the flared proximal end 222 of the cannula 222 and attaching the cap 269 to the drum. Alternatively, the threaded distal end 276 and cap 269 can be omitted and the proximal end 222 of the cannula 220 can be integrated with, or fixedly attached to, the drum 267 (e.g., insert molding). The drum 267 has an outer diameter slightly less than the inner diameter of the cavity 263. Both the drum 267 and the cannula 220 are slidably disposed over the introducer 208 and the spring 268 is disposed in a slightly compressed state between the distal end of the drum 267 and the interior surface 253 of the head member 240.

The spring 268 can be manufactured out of various materials and can have varying compressed and uncompressed lengths. An exemplary spring 268 is illustrated as a compression spring, which exerts a force resisting compression proportional to the distance the spring has been compressed. While the illustrated delivery system 200 includes a single spring 268 in a slightly compressed state, any suitable type and number of springs can be included in a delivery system in any suitable state, and skilled artisans will be able to select an appropriate type and number of springs for inclusion in a delivery system according to a particular embodiment based on various considerations, including the intended use of the delivery system, the expected number of uses of the delivery system, and the pressure required to retract the cannula after it has been advanced to release the ventilation tube. Examples of suitable numbers of springs include one, two, three and any other number determined suitable for a particular application.

The rocker arm 265 is pivotally attached to the housing within the elongate aperture 264 by a pin 266 and has a first portion 278 that partially extends out of the elongate aperture 264 and a second portion 279 that partially extends into the cavity 263. The second portion 279 of the rocker arm 265 splits over the introducer 208 and has a distal surface in communication with the proximal end of the drum 267.

The finger retraction handle 290 is a tubular member comprising two finger flanges 292, a proximal end 293, and a distal end 294. The finger retraction handle 290 is slidably disposed on the housing 260 between the proximal edge 252 of the head member 240 and the first portion 278 of the rocker arm 265. The finger retraction handle 290 has an inner diameter slightly larger than the outer diameter of the housing 260 and an outer diameter sized to provide a thickness sufficient to interact with the first portion 278 of the rocker arm 265 and the proximal edge 252 of the head member 240. The two finger flanges 292 are disposed near the proximal end 293 of the finger retraction handle 290 and extend outwardly away from the outer diameter of the finger retraction handle 290 and have a length and width sufficient to receive a user's fingers. While two finger flanges 292 have been illustrated and described, the finger retraction handle 290 can include a single finger flange, and skilled artisans will be able to select a suitable number of finger flanges according to a particular embodiment based on various considerations, including the intended use of the delivery system, and the intended use of the ventilation tube.

While the head member 240, housing 260, and finger retraction handle 290 have been described as having a particular configuration, the head member 240, housing 260, and finger retraction handle 290 can comprise various other configurations, and skilled artisans will be able to select an appropriate configuration for the head member, housing, and finger retraction handle based on various considerations, including the intended use of the delivery system, and the configuration of the head member, housing, and/or finger retraction handle.

The delivery system 200 has a first unextended position and a second extended position which allows for the cannula 220 to be moveable along the introducer between a first position and a second position. In the first unextended position, the spring 268 maintains pressure on the distal end of the drum 267, which forces the second portion 279 of the rocker arm 265 proximally. This results in the first portion 278 of the rocker arm 265 being forced distally and forcing the proximal end 293 of the finger retraction handle 290 distally. In this first position, the cannula 220 is located proximal to the proximal end of the ventilation tube 300, or it can contact the proximal end of the ventilation tube 300. In the second extended position, force is exerted on the finger flanges 292 in the proximal direction (e.g., by a physician placing his thumb on the proximal end 261 of the housing 260 and two fingers on a distal portion of the finger flanges 292) and the finger retraction handle 290 pushes the first portion 278 of the rocker arm 265 proximally forcing the second portion 279 of the rocker arm 265 distally. This motion forces the drum 267 and affixed cannula 220 distally applying a force on the proximal end of the ventilation tube 300, and ultimately pushing the ventilation tube 300 off of the introducer 208. In this second position, the cannula is moved along the introducer 208 distally to release the ventilation tube from the introducer 208. Upon releasing the proximal force on the finger flanges 292, the spring 268 exerts pressure on the distal end of the drum 267, returning the rocker arm 265, drum 267, affixed cannula 220, and finger retraction handle 290 back to the first unextended position.

The distance between the finger flanges 292 and the proximal end 261 of the housing 260 is advantageously sized to fit in a user's hand, limiting loss of a user's motor skill when using the delivery system 200. The proximal end 261 of the housing 260 defines a surface for receiving the thumb of a user and can include an indentation and/or taper allowing the housing 260 to rest in the hand of a user.

The head member 240, housing 260, finger retraction handle 290, drum 267, and rocker arm 265, can be manufactured from various materials, such as polymeric materials, and can be formed using various methods, such as injection molding. While various configurations, materials, and methods of forming the head member 240, housing 260, finger retraction handle 290, drum 267, and rocker arm 265, have been described, skilled artisans will be able to select suitable configurations, materials, and methods of forming the head, housing, finger retraction handle, drum, and rocker arm, according to a particular embodiment based on various considerations, including the intended use of the delivery system, and the configuration of the introducer and/or cannula.

Figure 18:
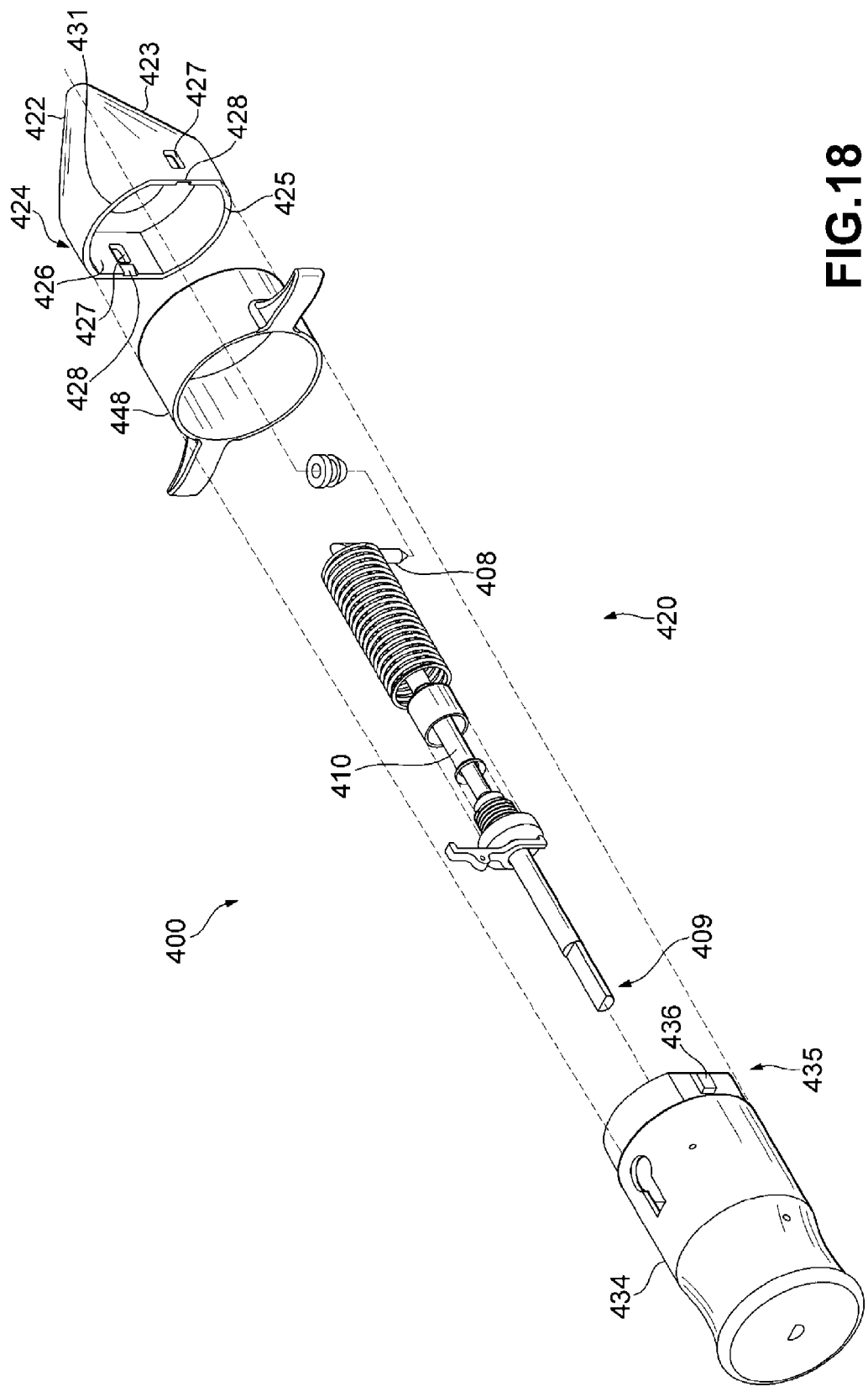
FIG. 18 is an exploded view of another exemplary delivery system and associated ventilation tube.

FIG. 18 is an exploded view of another exemplary delivery system 400 and associated ventilation tube 300. The delivery system 400 illustrated in FIG. 18 is similar to the delivery system 200 illustrated in FIGS. 15 through 17, except as detailed below. The delivery system 400 comprises an introducer 408, a cannula 410, and a handle 420. The ventilation tube 300 is similar to that described above with respect to FIG. 13A. While the illustrated delivery system 400 includes a ventilation tube 300 similar to that illustrated in FIG. 13A, any suitable ventilation tube can be used in combination with the delivery system 400, and skilled artisans will be able to select an appropriate ventilation tube for inclusion with a delivery system according to a particular embodiment based on various considerations, including the intended use of the delivery system, the intended use of the ventilation tube, and others.

The handle 420 is disposed on the proximal end 409 of the introducer 408 and comprises a head member 422, a housing 434, and a finger retraction handle 448. The head member 422 is disposed on a distal end of the housing 434 and has a tapered distal end 423, a proximal end 424, and a proximal edge 425. The head member 422 also defines a lumen 426 extending through the length of the head member 422, two apertures 427, and two recesses 428. The two apertures 427 extend through the wall of the head member 422 and provide access to the lumen 426.

The tapered distal end 423 extends from the distal end of the head member 422 proximally and away from the center of the lumen 426 to the proximal end 424. The proximal end 424 of the head member 422 has an inner diameter 431 and depth sufficient to receive a portion of the distal end 436 of the housing 434.

The housing 434 has a varying outer diameter and comprises a distal end 435 adapted to be received by a portion of the head member 422 and includes two projections 436. The projections 436, apertures 427, and recesses 428 are adapted to provide a snap fit connection between the housing 434 and the head member 422.

While a particular type of snap fit and two apertures 427, recesses 428, and projections 436 have been described and illustrated, various other types of snap fits and numbers of apertures, recesses, and projections can be used, and skilled artisans will be able to select a suitable configuration for the snap fit and number of apertures, recesses, and projections according to a particular embodiment based on various considerations, including the intended use of the delivery system, and the configurations of the head member and/or housing. Examples of numbers of apertures, recesses, and projections include one, two, three, four, five and any number considered suitable for a particular application.

Figure 19:
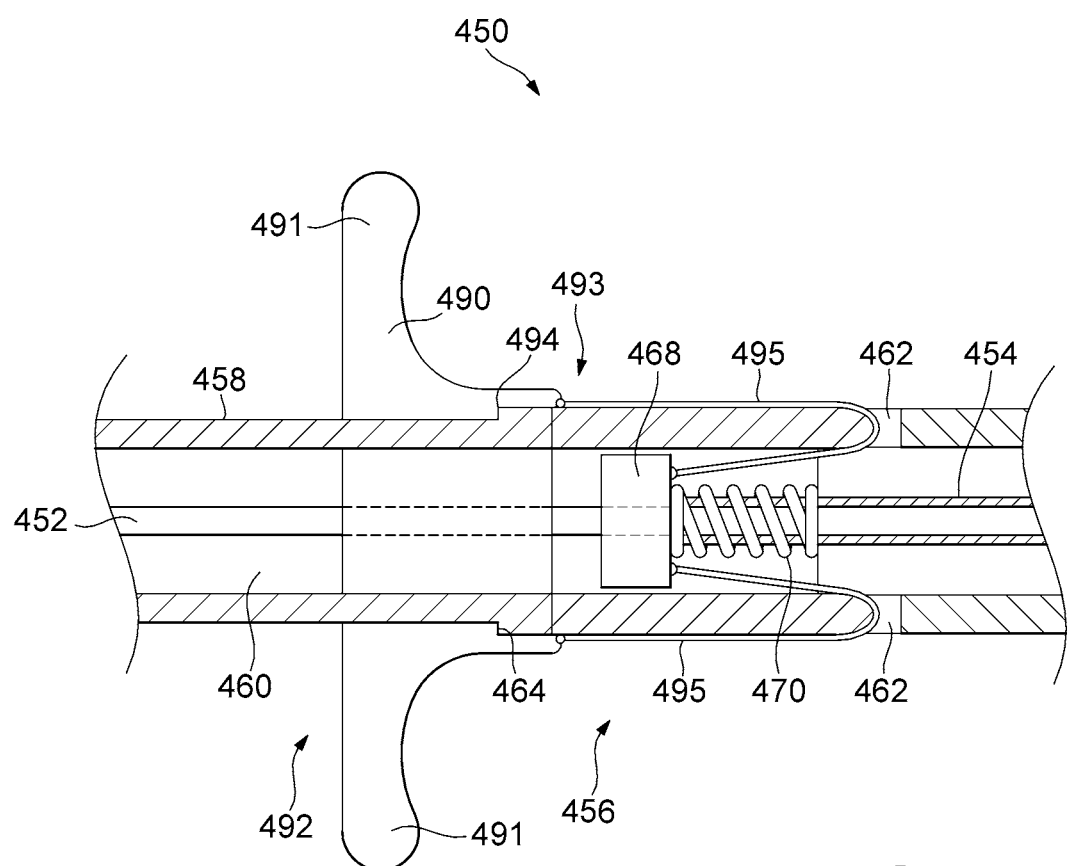
FIG. 19 is a sectional view of a portion of the handle of another exemplary delivery system.

FIG. 19 is a sectional view of a portion of the handle of another exemplary delivery system 450. The delivery system 450 illustrated in FIG. 19 is similar to the delivery system 200 illustrated in FIGS. 15 through 17, except as detailed below. The delivery system 450 comprises an introducer 452, a cannula 454, and a handle 456.

In contrast to delivery system 200, which includes a rocker arm and pin assembly, the delivery system 450 includes a wire assembly to advance the drum distally. The handle 456 is disposed on the proximal end of the introducer 452 and comprises a head member (not shown), a housing 458, and a finger retraction handle 490. The housing 458 comprises a cavity 460, two apertures 462, and a ridge 464. The two apertures 462 extend through the housing 458 and provide access to the cavity 460 which extends through the length of the housing 458 and contains a drum 468 and spring 470. The ridge 464 of the housing 458 is located proximal to the apertures 462.

The finger retraction handle 490 is slidably disposed over the housing 458 and comprises a tubular member with two finger flanges 491, a proximal end 492, a distal end 493, and a ridge 494. The ridge 494 of the finger retraction handle 490 mirrors the ridge 464 of the housing.

Two flexible lines 495 are connected to the distal end 493 of the finger retraction handle 490, extend through the apertures 462, and are connected to the distal end of the drum 468. The length of the flexible lines 495 can be equal to, or slightly greater than or less than, the sum of the distance from the distal end 493 of the finger retraction handle 490 to the apertures 462, the depth of the apertures 462, and the distance from the apertures 462 to the distal end of the drum 468. While a particular length and number of flexible lines 495 has been described and illustrated, any suitable length and number of flexible lines can be included, and skilled artisans will be able to select a suitable length and number of flexible lines according to a particular embodiment based on various considerations, including the configuration of the cannula, housing, apertures, and finger retraction handle.

The delivery system 450 has a first unextended position and a second extended position. In the first unextended position, the spring 470 maintains pressure on the distal end of the drum 468, which pulls the flexible lines 495 proximally within the cavity 460. This results in the finger retraction handle 490 being forced distally to a position where the ridge 494 of the finger retraction handle 490 is in communication with the ridge 464 of the housing 458. In the second extended position, force is exerted on the finger retraction handle 490 in the proximal direction (e.g., by a physician placing his thumb on the proximal end of the housing and two fingers on a distal portion of the finger flanges) and the finger retraction handle 490 pulls the flexible lines 495 distally within the cavity 460. This motion forces the drum 468 and affixed cannula 454 distally applying a force on the proximal end of the ventilation tube, and ultimately pushing the ventilation tube off of the introducer 452. Upon releasing the proximal force on the finger retraction handle 490, the spring 470 exerts pressure on the distal end of the drum 468, returning the drum 468, affixed cannula 454, and finger retraction handle 490 back to the first position.

Figure 20:
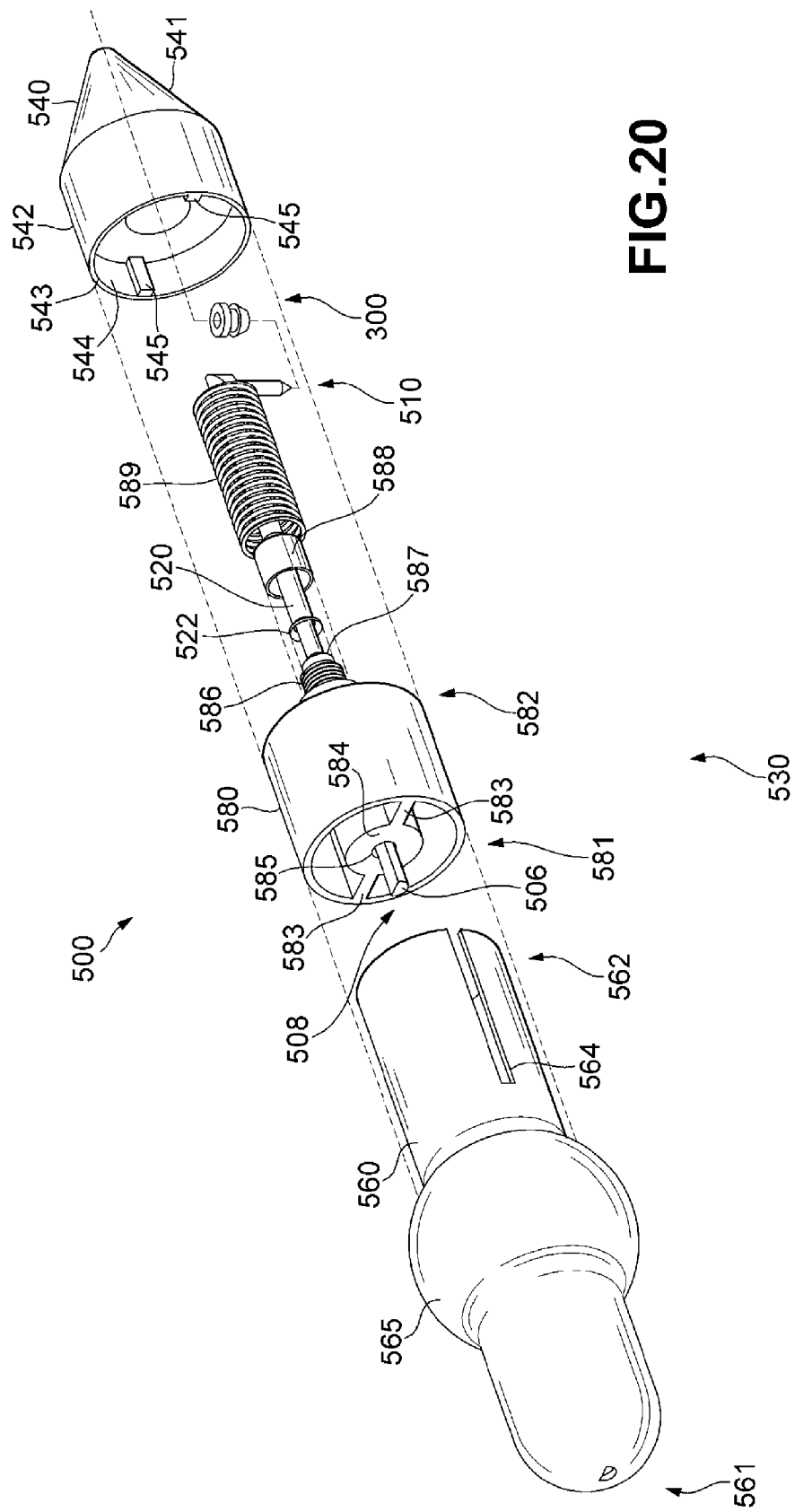
FIG. 20 is an exploded view of another exemplary delivery system and associated ventilation tube.

FIG. 20 is an exploded view of another exemplary delivery system 500 and associated ventilation tube 300. The delivery system 500 illustrated in FIG. 20 is similar to the delivery system 200 illustrated in FIGS. 15 through 17, except as detailed below. The delivery system 500 comprises an introducer 506, a cannula 520, and a handle 530. The ventilation tube 300 is similar to that described above with respect to FIG. 13A. While the illustrated delivery system 500 includes a ventilation tube 300 similar to that illustrated in FIG. 13A, any suitable ventilation tube can be used in combination with the delivery system 500, and skilled artisans will be able to select an appropriate ventilation tube for inclusion with a delivery system according to a particular embodiment based on various considerations, including the intended use of the delivery system, the intended use of the ventilation tube, and others.

The introducer 506 comprises an elongate rigid structure with a proximal end 508 and a distal end 510. The cannula 520 is slidably disposed over the introducer 508 and has a flared proximal end 522 disposed within the handle 530. The handle 530 is disposed on the proximal end 508 of the introducer 506 and comprises a head member 540, a housing 560, and a slider 580. The head member 540 is disposed on a distal end of the housing 560 and has a tapered distal end 541, an annular proximal end 542, and a proximal edge 543. The head member 540 also defines a lumen 544 extending through the length of the head member 540 and two protrusions 545 extending into lumen 544. The tapered distal end 541 extends proximally and away from the center of the lumen 544 to the annular proximal end 542 which extends proximally to the proximal edge 543. The annular proximal end 542 of the head member 540 has an inner diameter and depth sufficient to receive a portion of the distal end 562 of the housing 560.

The housing 560 comprises a proximal end 561 and a distal end 562 and defines two tracks 564 and an ergonomic grip 565. The tracks 564 are configured to receive the two protrusions 545 of the head member 540. The distal end 562 of the housing 560 has an outer diameter and length sufficient to be received by, and attached to, a portion of the head member 540.

The slider 580 comprises a proximal end 581, a distal end 582, two connectors 583 connecting a center tubular member 584. The center tubular member 584 defines a lumen 585 and has a threaded distal end 586 that includes a taper 587 that mirrors the flared proximal end 522 of the cannula 520. The center tubular member 584 is attached to the flared proximal end 522 of the cannula 520 by sliding a cap 588, which has a threaded inner diameter, over the cannula 520 and attaching the cap 588 to the threaded distal end 586 of the center tubular member 584. Alternatively, the threaded distal end 586 and cap 588 can be omitted and the proximal end 522 of the cannula 520 can be integrated with the distal end of the center tubular member 584.

The slider 580 has connectors 583 slidably disposed with the tracks 564 of the housing 560 and is adapted to be moveable within the tracks 564 between the proximal edge 543 of the head member 540 and the proximal end of the tracks 564. A spring 589 is disposed between the distal end 582 of the slider 580 and the interior surface of the head member 540. Both the slider 580 and the cannula 520 are slidably disposed over the introducer 506, which extends through the spring 589 and slider 580 and has a proximal end 508 affixed to the housing 560.

Attaching the housing 560 to the head member 540 can be accomplished using various methods, and skilled artisans will be able to select an appropriate method according to a particular embodiment based on various considerations, including the intended use of the delivery system, and the intended use of the ventilation tube. Example methods of attaching the head member 540 to the housing 560 include snap fitting, adhesively affixing, using a set screw and/or pin, insert molding, and any other method considered suitable for a particular application.

The delivery system 500 has a first unextended position and a second extended position. In the first unextended position, the spring 589 maintains pressure on the distal end of the slider 580, which forces the distal end 524 of the affixed cannula 520 proximally. In the second extended position, force is exerted on the slider 580 in the distal direction and the slider 580 forces the affixed cannula 520 distally applying a force on the proximal end of the ventilation tube 300, and ultimately pushing the ventilation tube 300 off of the introducer 506. Upon releasing the proximal force on the slider 580, the spring 589 exerts pressure on the distal end of the slider 580, returning the affixed cannula 520 and slider 580 back to the first position.

Releasably connecting the ventilation tube 300 to the distal end of the delivery system can be accomplished using various configurations. Exemplary configurations are described below, but are not intended to be limiting in nature. The ventilation tube 300 is configured to have a resting diameter and a loaded diameter. The ventilation tube 300 defines a channel 312 that has a resting diameter when the ventilation tube is free of the introducer 208 and a loaded diameter when the ventilation tube is disposed on the introducer 208.

Figure 21:
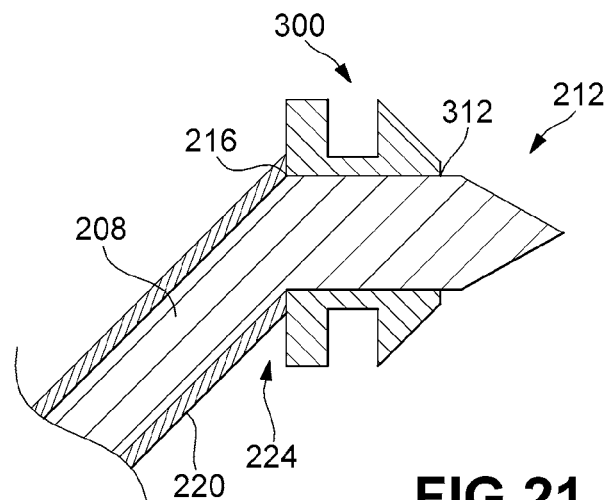
FIG. 21 is a sectional view of the distal end of the delivery system and associated ventilation tube illustrated in FIGS. 15 through 17.

FIG. 21 illustrates a sectional view of the distal end of the delivery system 200 and associated ventilation tube 300 illustrated in FIGS. 15 through 17. The distal end of the delivery system 200 provides for releasably disposing the ventilation tube 300 on the distal end 212 of the introducer 208 using an interference fit. The central channel 312 has a resting diameter when it is free of the introducer 208. When the ventilation tube 300 is loaded on the introducer 208, the central channel expands to its loaded diameter, advantageously providing an interference fit between the ventilation tube 300 and the introducer 208. Alternatively, the central channel 312 of the ventilation tube 300 can be, however, sized larger than the distal end of the introducer 208.

The ventilation tube 300 is received by the distal end 212 of the introducer 208 which has an introducer diameter sized slightly larger than inner diameter of the central channel 312, requiring the central channel 312 of the ventilation tube 300 to be forced onto the distal end 212 of the introducer 208 and expand from its resting diameter to its loaded diameter. The ventilation tube 300 is disposed on the introducer 208 distal to the bend 216. The bend 216 of the introducer 208 and/or the distal end 224 of the cannula 220 act as a stop for the ventilation tube 300. The outside diameter of the cannula 220 is greater than the loaded diameter of the ventilation tube 300. To release the ventilation tube 300, the delivery system 200 advances to the second extended position sliding the cannula 220 distally over the introducer 208 resulting in a force being exerted on the proximal end 316 of the ventilation tube 300, which is adapted to interact with the distal end 224 of the cannula 220. The distal end 224 of the cannula 220 can comprise a flexible material which allows the cannula 220 to advance over the bend 216. Once the force is sufficient to overcome the interference fit, the ventilation tube 300 is released from the distal end 212 of the introducer 208.

Figure 22:
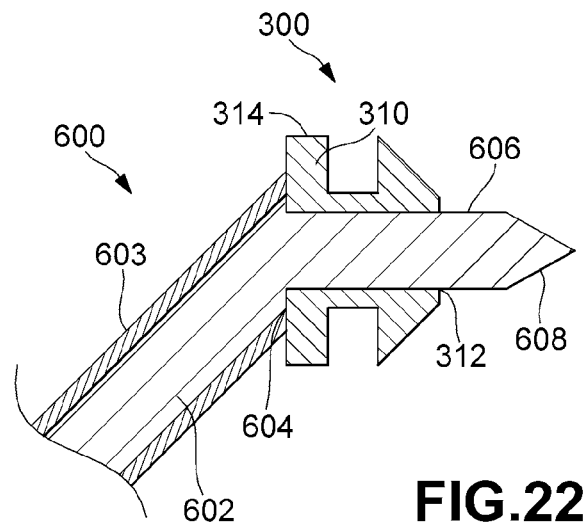
FIG. 22 is a sectional view of the distal end of another exemplary delivery system and associated ventilation tube.

FIG. 22 is a sectional view of the distal end of another exemplary delivery system 600 and associated ventilation tube 300. The introducer 602 comprises a first introducer diameter 604, a second introducer diameter 606, and a sharp distal tip 608. The second introducer diameter 606 is greater than, less than, or equal to, the resting diameter of the ventilation tube 300. When the second introducer diameter 606 is greater than the resting diameter of the ventilation tube 300, force is required to load the ventilation tube 300 onto the introducer 602. The first introducer diameter 604 is sized slightly larger than the loaded diameter of the central channel 312 of the ventilation tube 300 and the introducer 602 defines a shoulder that transitions from the first introducer diameter 604 to the second introducer diameter 606. The length of the second introducer diameter 606 is sufficient to receive the ventilation tube 300 and allow the sharp distal tip 608 to be disposed distal to the ventilation tube 300. The difference between the first introducer diameter 604 and the second introducer diameter 606 is less than the difference between the outer diameter 314 of the flange 310 and the loaded diameter of the central channel 312 of the ventilation tube 300, leaving a contact surface on the proximal end of the ventilation tube 300 adapted to interact with the cannula 603.

Figure 23:
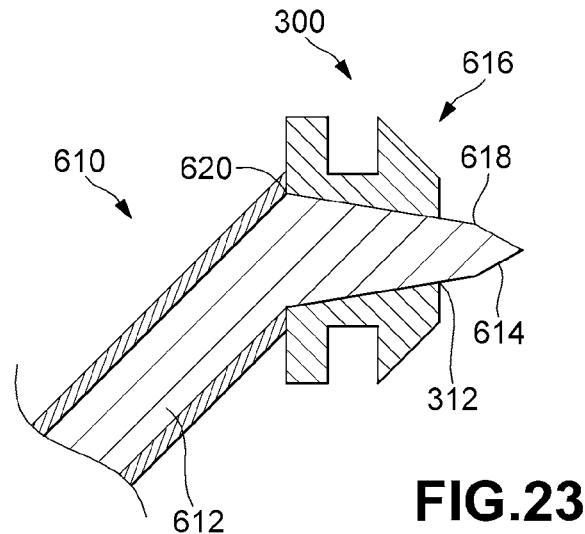
FIG. 23 is a sectional view of the distal end of another exemplary delivery system and associated ventilation tube.

FIG. 23 is a sectional view of the distal end of another exemplary delivery system 610 and associated ventilation tube 300. The introducer 612 comprises a sharp distal tip 614, tapered distal end 616, a first outer diameter 618, and a second outer diameter 620. The first outer diameter 618 is positioned proximal to the sharp distal tip 614 which gradually increases to the second outer diameter 620 which is proximal to the first outer diameter 618. The first outer diameter 618 is less than the resting diameter of the central channel 312 of the ventilation tube 300. The second outer diameter 620 is slightly larger than the resting diameter of the central channel 312 of the ventilation tube 300, requiring the ventilation tube 300 to be forced onto the introducer 612.

Figure 24:
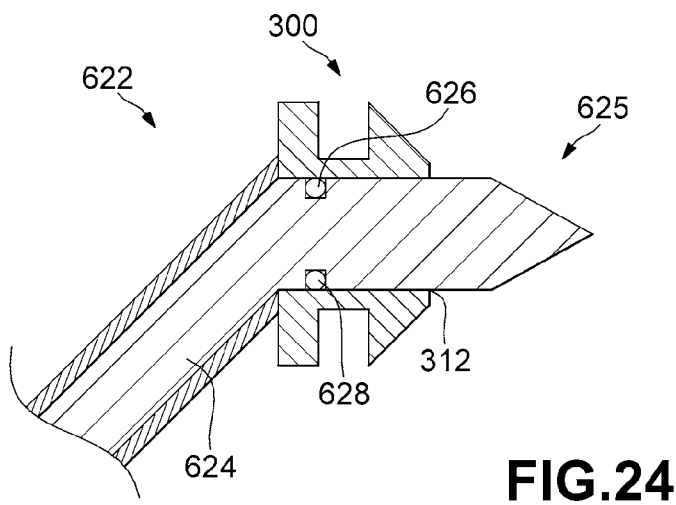
FIG. 24 is a sectional view of the distal end of another exemplary delivery system and associated ventilation tube.

FIG. 24 is a sectional view of the distal end of another exemplary delivery system 622 and associated ventilation tube 300. The introducer 624 is similar to that illustrated in FIG. 21 but defines a circumferential recess 628 located proximal to the distal end 625 of the introducer 624 and comprises a flexible o-ring 626 disposed within the recess 628. The o-ring 626 is sized to be larger than the depth of the recess 628 and have an outside diameter larger than the resting diameter of the channel 312 of the ventilation tube 300 to provide an interference fit between the o-ring 626 and the central channel 312 of the ventilation tube 300. The o-ring 626 advantageously allows for wider manufacturing tolerances of the central channel 312 of the ventilation tube 300 and provides consistent resistance across a wider range of interference fits. The o-ring configuration can be used in combination with the other distal end configurations described with respect to FIGS. 21 through 26, or independent of these configurations. For example, the o-ring configuration can be used in combination with an introducer that does or does not include a reduced diameter, and/or a tapered distal end.

Figure 25:
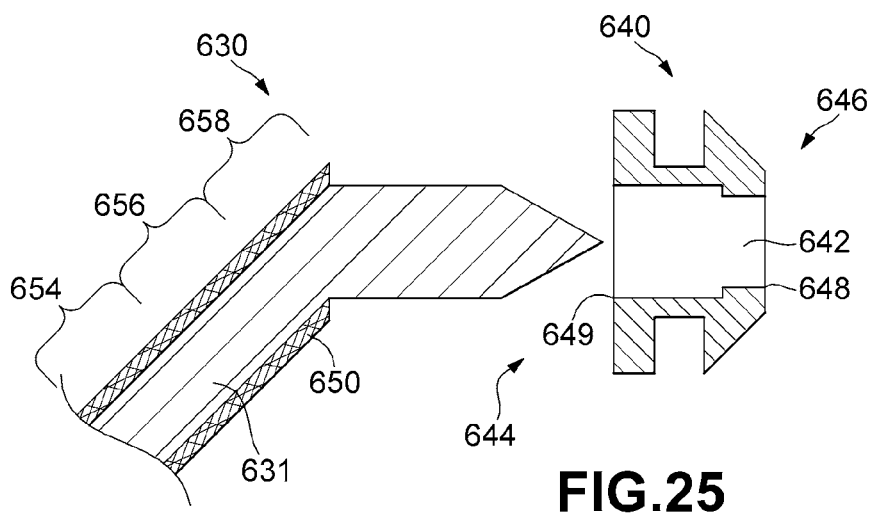
FIG. 25 is a sectional view of the distal end of another exemplary delivery system and an alternative exemplary ventilation tube.

Various configurations of the ventilation tube 300 can be utilized in combination with the exemplary embodiments described herein. FIG. 25 is a sectional view of the distal end of another exemplary delivery system 630 and alternative exemplary ventilation tube 640. The delivery system 630 comprises an introducer 631 and a cannula 650.

The delivery system 630 provides for releasably attaching the ventilation tube 640 to the introducer 631 using an interference fit. The ventilation tube 640 defines a central channel 642 and comprises a proximal end 644 and a distal end 646. The central channel 642 has a first resting diameter 648 and a second resting diameter 649. The first resting diameter 648 is located on the distal end 646 of the ventilation tube 640 and is sized smaller than the second resting diameter 649. The channel defines a shoulder that transitions from the first resting diameter 648 to the second resting diameter 649. The introducer diameter 631 is sized smaller than the second resting diameter 649 of the ventilation tube 640 and larger than the first resting diameter 648 of the ventilation tube 640. This configuration allows for the interference fit to be limited to the distal end 646 of the ventilation tube 640.

The cannula 650 includes a proximal portion 654, an intermediate portion 656, and a distal portion 658. Each of the proximal 654, intermediate 656, and distal portions 658 is formed of a different material. For example, the proximal portion 654 can be formed of a polymer, the intermediate portion 656 can be formed of a flexible material, and the distal portion 658 can be formed of a rigid material (e.g., metal). While the cannula has been described as having a proximal portion 654, an intermediate portion 656, and a distal portion 658 formed of different materials, skilled artisans will be able to select appropriate material to include with the cannula, or portions thereof, according to a particular embodiment based on various considerations, including the configuration of the distal end of the introducer, the configuration of the central channel of the ventilation tube, and the intended use of the delivery system.

Figure 26:
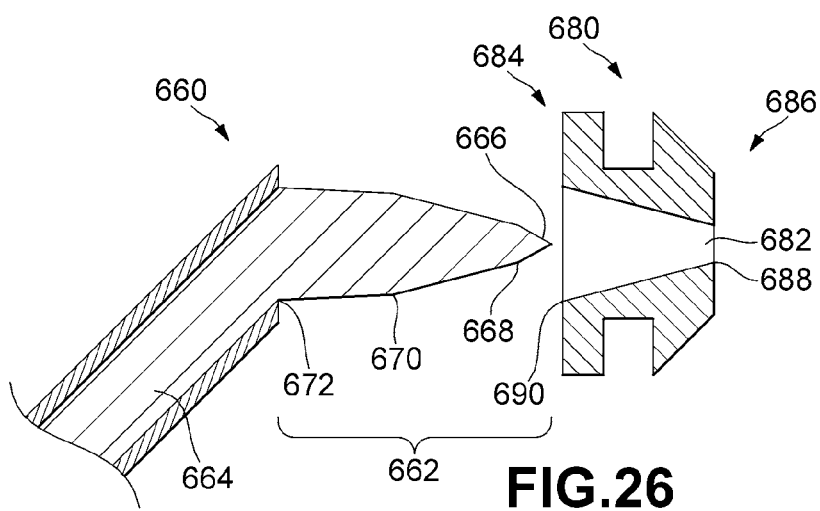
FIG. 26 is a sectional view of the distal end of another exemplary delivery system and another alternative ventilation tube.

FIG. 26 is a sectional view of the distal end of another exemplary delivery system 660 and another alternative ventilation tube 680. The introducer 664 has a sharp distal tip 666 and a multiple tapered distal end 662. The tapered distal end 662 has a first introducer diameter 668, a second introducer diameter 670, and a third introducer diameter 672. The first introducer diameter 668 is positioned proximal to the sharp distal tip 666 and gradually increases to the second introducer diameter 670, which gradually increases to the third introducer diameter 672.

The delivery system 660 provides for releasably attaching the ventilation tube 680 to the introducer 664 using an interference fit. The ventilation tube 680 defines a tapered central channel 682 and comprises a proximal end 684 and a distal end 686. The tapered central channel 682 has a first resting diameter 688 and a second resting diameter 690 and tapers from the proximal end 684 to the distal end 686. The first resting diameter 688 is located on the distal end 686 of the ventilation tube 680 and is sized smaller than the second resting diameter 690. The first 668 and/or second 670 introducer diameter 664 is sized smaller than the second resting diameter 690 of the ventilation tube 680 and larger than the first resting diameter 688 of the ventilation tube 680. This configuration allows for the interference fit to be limited to the distal end 686 of the ventilation tube 680.

Limiting the interference fit to the distal end 686 of the ventilation tube 680 advantageously allows for the thinnest portion of the ventilation tube 680 to be in contact with the introducer 664, allowing for flexibility of the ventilation tube 680. While the central channel 682 has been described and illustrated as having a tapered configuration from the proximal end 684 to the distal end 686, the taper can be configured to limit the interference fit to the proximal end 684.

FIG. 27 is a sectional view of another exemplary delivery system 700 and associated ventilation tube 800. The delivery system 700 comprises an introducer 708, a gripping member 720, a cannula 730, and a handle 740. The introducer 708 is an elongate rigid structure and comprises a sharp distal tip 710, a proximal end 712, and a distal end 714 adapted to receive the ventilation tube 800.

The gripping member 720 is a tubular member disposed over the introducer 708 and comprises a proximal end 721 and furcated distal end 722 having multiple grasping elements 724 which naturally gravitate away from the introducer 708. The cannula 730 is slidably disposed over the a portion of the gripping member 720 and introducer 708 and comprises a flexible tubular structure with a proximal end 731, and a distal end 732. The proximal end 731 of the cannula 730 is disposed within the handle 740 and the distal end 732 of the cannula 730 is disposed proximal to the distal ends of the gripping elements 724.

The handle 740 is disposed on the proximal end 712 of the introducer 708 and comprises a head 750, a housing 760, and a finger retraction handle 790. The head 750 is disposed on a distal end of the housing 760 and comprises an annular proximal end 751, a tapered distal end 752, a lumen 753, and a proximal edge 756. The tapered distal end 752 extends proximally and away from the lumen 753 to the annular portion 751 that extends proximally to the proximal edge 756. The annular proximal end 751 of the head 750 has an inner diameter and depth sufficient to receive a portion of the distal end of the housing 760.

The housing 760 comprises a cavity 763, two elongate apertures 764, two connecting members 765, a drum 766, and a spring 767. The distal end of the housing 760 has an outer diameter and length sufficient to be received by a portion of the annular proximal end 751 of the head 750 and includes a ridge 771 which engages the proximal edge 756 of the of the head 750. The elongate apertures 764 extend through the housing 760 and provide access to the cavity 763. The cavity 763 extends through the length of the housing, defines a first lumen 768 and a second lumen 769 and contains the drum 766 and spring 767. The second lumen 769 has a diameter which is less than the first lumen 768 which defines a reduced step portion 770. The gripping member 720 extends through the cavity 763, the first lumen 768, the drum 766, spring 767 and has a proximal end 721 that engages and is adhesively affixed to reduced step portion 770. The introducer 708 extends through the gripping member 720 and is adhesively affixed within the second lumen 769. The drum 766 is affixed to the proximal end 731 of the cannula 730 and both the drum 766 and cannula 730 are slidably disposed over the gripping member 720 and introducer 708. The drum 766 has an outer diameter slightly less than the inner diameter of the cavity 763. The spring 767 is disposed between the proximal end of the cavity 763 and the proximal end of the drum 766.

While the gripping member 720 and introducer 708 have been described as adhesively affixed within the housing 760, other suitable methods of attachment, either releasably or permanently, can be used, and skilled artisans will be able to select suitable methods of attachment according to a particular embodiment based on various considerations, including the intended use of the delivery system, and the intended use of the ventilation tube.

The finger retraction handle 790 comprises a tubular member having two finger flanges 792. The finger retraction handle 790 is slidably disposed over the housing 760 and is connected to the drum 766 by the connecting members 765 which extend through the elongate apertures 764 of the housing. The two finger flanges 792 extend outwardly away from the finger retraction handle 790 a length and width sufficient to receive a user's fingers.

In the first position, the ventilation tube 800 is releasably connected to the distal end 714 of the introducer 708 by the grasping elements 724 which are forced towards the introducer 708 by the spring 767 maintaining pressure on the proximal end of the drum 766. This pressure pushes the affixed cannula 730 over a portion of the distal end 722 of the gripping member 720 and a proximal portion of the grasping elements 724. In the second position, force is exerted on the finger flanges 792 in a proximal direction, and the attached drum 766 is forced proximally which retracts the cannula 730 from the grasping elements 724. The proximal movement of the cannula 730 removes the distal end 732 of the cannula 730 off of the grasping elements 724, allowing the grasping elements 724 to expand to their natural position away from the introducer 708 releasing the ventilation tube 800. Upon releasing the proximal force on the finger flanges 792, the spring 767 exerts pressure on the proximal end of the drum 766, forcing the drum 766, affixed cannula 730, finger retraction handle 790, and grasping elements 724 back to the first position.

To provide sufficient force to close the grasping elements 724, the cannula 730 can include a distal end 732 made of a semi-rigid or rigid material. The gripping member 720 and grasper elements 724 can be manufactured out of any suitable rigid material, such as, a memory alloy, spring metal, tempered steel, and the like. While the gripping member 720 and grasping elements 724 have been described as being made from a particular material, skilled artisans will be able to select a suitable material for the gripping member and grasping elements according to a particular embodiment based on various considerations, including the intended use of the delivery system, the configuration of the distal end of the gripping member, the configuration of the ventilation tube, and others.

Releasably connecting the ventilation tube 800 to the distal end of the exemplary delivery system illustrated in FIG. 27 can be accomplished using various ventilation tube 800 configurations. Exemplary configurations are described below, but are not intended to be limiting in nature.

FIG. 27 includes a ventilation tube 800 which is similar to that illustrated in FIG. 13A, but comprises a proximal end 802, a distal end 804, conical or frusto-conical retaining member 806, a shoulder 808, a first flange 810, a central channel 812 extending through the ventilation tube 800, and a second flange 814 disposed proximal to the first flange 810. The second flange 814 is spaced from the first flange 810 a distance equal to or slightly larger than the width of the grasping elements 724 which grasp the ventilation tube 800 between the first flange 810 and the second flange 814.

FIG. 28 is a side view of the distal end of the delivery system 700 illustrated in FIG. 27 and includes an alternative ventilation tube 900. The ventilation tube 900 is similar to that illustrated in FIG. 13A, but comprises a proximal end 902, a distal end 904, conical or frusto-conical retaining member 906, a shoulder 908, a flange 910, a central channel 912 extending through the ventilation tube 900, and multiple cavities 914. The cavities 914 receive a portion of the grasping elements 724 and allow for releasably connecting the ventilation tube 900 to the delivery system 700. The configuration and depth of the cavities 914 mirrors a portion of the grasping elements 724. While the illustrated ventilation tube 900 includes multiple cavities with configurations that mirror a portion of the grasping elements 724, any suitable configuration and number of cavities can be included, and skilled artisans will be able to select an appropriate configuration and number of cavities for inclusion in a delivery system according to a particular embodiment based on various considerations, including the intended use of the delivery system, the type of procedure being performed, the configuration of the distal end of the handle, and others.

Various compositions can be used to manufacture the ventilation tubes described herein. For example, the ventilation tube can be formed of any degradable material, polymeric material, or the like. In addition, the ventilation tube, introducer, and/or cannula can be radiopaque or include radiopaque markers to aid the physician in positioning the ventilation tube at a treatment site. For example, portions of the ventilation tube, introducer, and/or cannula can include a radiopaque material that can be identified by X-ray. Examples of radiopaque material include, but are not limited to, highdensity metals such as platinum, iridium, gold, silver, tantalum, radiopaque polymeric compounds, and the like.

While the delivery systems described above have included a spring to advantageously return the cannula to the first position, the spring can be omitted, and skilled artisans will be able to select a suitable configuration for the delivery system according to a particular embodiment based on various considerations, including the intended use of the delivery system, the intended use of the ventilation tube, and the configuration of the handle.

FIGS. 29 and 30 illustrate a partial sectional view of another exemplary delivery system 1000 and associated ventilation tube 1100. The delivery system comprises an introducer 1010, a handle 1020, a slider 1030, a wire 1040, and a flexible tube 1050. The ventilation tube 1100 is similar to that described in FIG. 13A, but comprises a proximal end 1102, a distal end 1104, a conical or frusto-conical retaining member 1106, a shoulder 1108, a flange 1110, a central channel 1112 extending through the ventilation tube 1100, and two apertures 1114 disposed within the central channel 1112 between the flange 1110 and frusto-conical retaining member 1106.

The introducer 1010 is a tubular member and has a proximal end 1011 and a distal end 1012 and defines an elongate proximal aperture 1013, two distal apertures 1014, and a chamber 1015. A sharp distal tip 1016 is attached to the distal end 1012 of the introducer 1010. The elongate proximal aperture 1013 and the two distal apertures 1014 extend through the wall of the introducer 1010 and provide access to the chamber 1015. The two distal apertures 1014 are located proximal to the sharp distal tip 1016. The sharp distal tip 1016 is fixedly attached to the distal end 1012 of the introducer. The sharp distal tip 1016 can be, however, integrated with or releasably attached to the introducer 1010.

The handle 1020 is disposed on, and fixedly attached to, the proximal end 1011 of the introducer 1010 and comprises an elongate member. The handle 1020 can be, however, integrally formed or releasably attached to the introducer 1010. The slider 1030 is slidably disposed within the elongate aperture 1012 of the introducer 1010. The slider 1030 comprises a first portion 1031 and a second portion 1032 connected by a connector 1033. The first portion 1031 has a diameter slightly smaller than the inner diameter of the chamber 1015 and includes an aperture 1034. The connector 1033 is sized slightly smaller than the elongate proximal aperture 1013 and extends through the elongate proximal aperture 1013 connecting the first 1031 and second portion 1032, which are sized larger than the elongate proximal aperture 1013.

The wire 1040 comprises a proximal end 1041 and a distal end 1042 having two attachment elements 1043. The proximal end 1041 is attached to the handle 1020 and extends through the aperture 1034 of the first portion 1031 of the slider 1030. The distal end 1042 branches into the two attachment elements 1043 proximal to the two distal apertures 1014 of the introducer 1010. The two attachment elements 1043 are in communication with the two distal apertures 1014 and naturally gravitate away from the center of the chamber 1015.

The wire 1040 can be preformed and made of a semi-rigid or rigid material, however, skilled artisans will be able to select a suitable material for inclusion in a delivery system according to a particular embodiment based on various considerations, including the intended use of the delivery system, the intended use of the ventilation tube, and others. While a single wire 1040 has been described and illustrated as having two attachment elements 1043, any suitable number of flexible wires and attachment elements can be included, and skilled artisans will be able to select an appropriate number of wires and attachment elements according to a particular embodiment based on various considerations, including the configuration of the ventilation tube, and the intended use of the delivery system. Examples of suitable numbers of wires and attachment members include one, two, three, four and any number considered suitable for a particular application.

The flexible tube 1050 is slidably disposed over the wire 1040 and comprises a proximal end 1051 attached to a distal surface of the first portion 1031 of the slider 1030 and a distal end 1052 that extends to the branching portion of the wire 1040.

The delivery system 1000 has a first configuration and a second configuration. The first configuration allows for a ventilation tube 1100 to be releasably affixed to the distal end 1012 of the introducer 1010 by the attachment elements 1043 extending within the apertures 1114 of the ventilation tube 1100. The second configuration withdraws the attachment elements 1043 from the apertures 1114 in the ventilation tube 1100, releasing the ventilation tube 1100 from the introducer 1010. In the first configuration, the slider 1030 is positioned at the proximal end of the elongate proximal aperture 1013 which positions the flexible tube 1050 slightly proximal to the branching portion of the wire 1040. This configuration allows the attachment elements 1043 to extend through the two distal apertures 1014 of the introducer 1010 and enter the two apertures 1114 of the ventilation tube 1100, providing a mechanism for releasably attaching the ventilation tube 1100 onto the distal end 1012 of the delivery system 1000. In the second configuration the slider 1030 is pushed distally within the elongate proximal aperture 1013, which advances the flexible tube 1050 past the branching portion of the wire 1040 retracting the attachment members 1043 from the two apertures 1114 in the ventilation tube 1100. This releases the ventilation tube 1100 from the introducer 1010.

Various methods of treating a sinus cavity are described herein. An initial step comprises attaching a ventilation tube to the distal end of a delivery system. Another step comprises advancing the distal end of the delivery system into the nostril to a point of treatment. Another step comprises inserting the ventilation tube at a point of treatment (e.g., lateral sinus wall). Another step comprises releasing the ventilation tube from the distal end of the delivery system. Another step comprises removing the distal end of the delivery system from the nostril. Another step comprises advancing the distal end of a catheter (e.g., a irrigation, infusion, and/or balloon catheter) through the channel of the ventilation tube such that the distal end of the catheter is in the targeted sinus cavity. Alternatively, the distal end of the catheter is advanced partially into the channel such that the distal end of the catheter is positioned within the channel of the ventilation tube. Another step comprises introducing an irrigation fluid or drug into the targeted sinus cavity. This step can be accomplished by passing the fluid or drug through the catheter while the distal end of the catheter is disposed in the targeted sinus cavity or in the channel of the ventilation tube. Alternatively, this step can be accomplished by passing another catheter through the previously placed catheter, connecting another catheter to the previously placed catheter, or other similar approach. Another step comprises withdrawing the catheter(s) from the channel of the ventilation tube. Another step comprises removing the ventilation tube from the point of treatment, if desired.

Additional, and/or alternative, steps can be included within the above described method. For example, the step of introducing an irrigation fluid or drug into the targeted sinus cavity can alternatively comprise inflating a balloon on the catheter. This step can be accomplished by passing a material through the catheter to inflate the balloon while the distal end of the catheter is disposed in the targeted sinus cavity. Alternatively, this step can be accomplished by passing another catheter through the previously placed catheter and past the distal end of the previously placed catheter.

In an additional example, the step of advancing the distal end of a catheter through the channel of the ventilation tube such that the distal end of the catheter is in the targeted sinus cavity can alternatively comprise advancing the distal end of the catheter through a natural PMO. Alternatively, this step can be accomplished by passing another catheter through the previously placed catheter and past the distal end of the previously placed catheter. Another step comprises inflating a balloon on the catheter. This step can be accomplished by passing a material through the catheter to inflate the balloon while the distal end of the catheter is disposed within the PMO.

Any ventilation tube, including the ventilation tubes described herein, can be used to assist in performing the above-described method. For example, the method can comprise the use of a ventilation tube as described above and illustrated in FIGS. 2A, 2B, 13A, 13B, 25, 26, 27, 28, 29, 30, or any alternatives thereof. In addition, any delivery system, including the delivery systems described herein, can be used to assist in performing the above-described method. For example, the method can comprise the use of a delivery system as described above and illustrated in FIGS. 2A, 3, 6, 8, 11, 15, 18, 19, 20, 21, 22, 23, 24, 25, 26, 27, 29, or any alternatives thereof. Alternatively, the method can comprise the use of a catheter as described above and illustrated in FIG. 14.

The configurations described above relating to the handles, the distal end of the delivery system, and/or ventilation tube can be used in combination with one another, or individually, and skilled artisans will be able to select an appropriate delivery system according to a particular embodiment based on various considerations, including the intended use of the delivery system, the intended use of the ventilation tube, the configuration of the ventilation tube, and others. Examples of suitable combinations of delivery systems include, but are not limited to, an introducer and/or ventilation tube interference fit used in combination with grasping members, an introducer and/or ventilation tube interference fit used in combination with a wire configuration, and/or a grasping member used in combination with a wire configuration.

In addition, any configuration of the ventilation tube can include material to be delivered to a patient. Exemplary materials are listed herein, and skilled artisans will be able to select suitable materials according to a particular embodiment based on various considerations, including the intended use of the ventilation tube, the configuration of the ventilation tube, the treatment being administered, and others.

Figure 31:
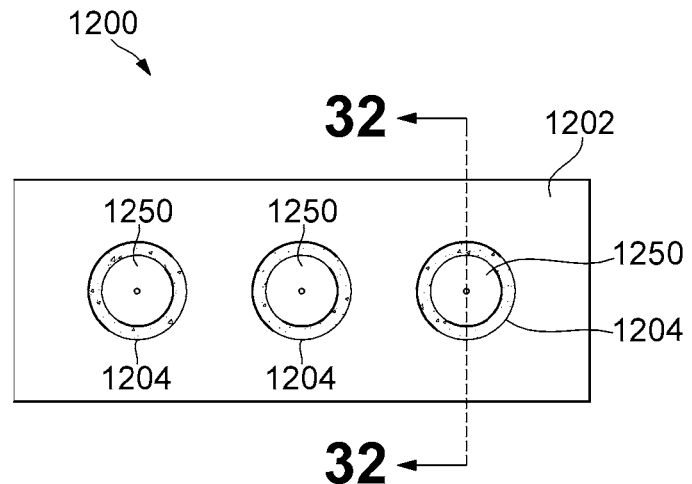
FIG. 31 is a top view of an exemplary ventilation tube container.
Figure 32:
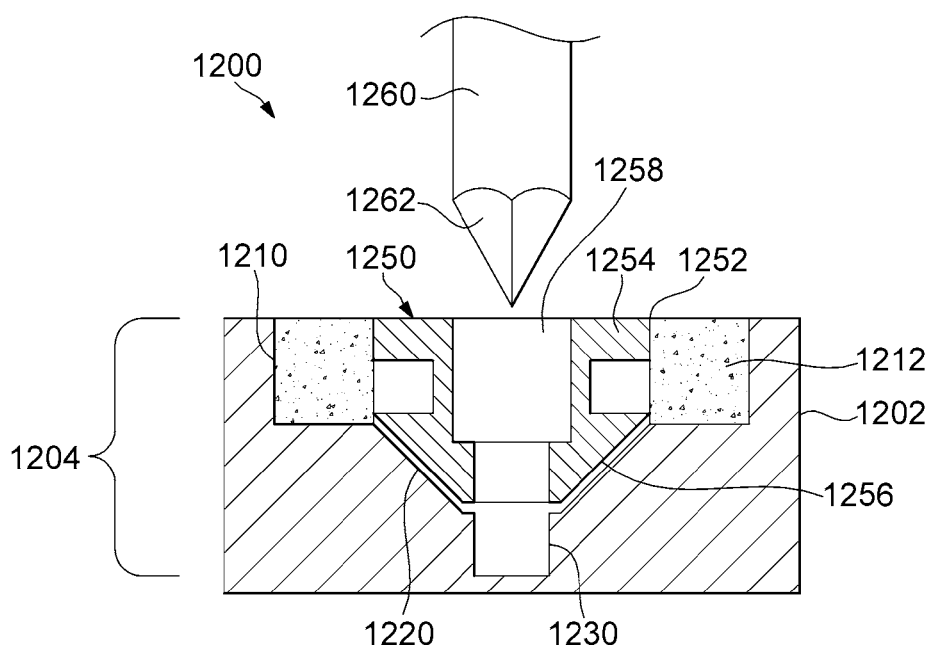
FIG. 32 is a sectional view of the ventilation tube container illustrated in FIG. 31, taken along lines 32-32.

An exemplary ventilation tube container 1200 is illustrated in FIGS. 31 and 32. The ventilation tube container 1200 comprises an elongate rigid body 1202 defining multiple independent recesses 1204 housing a ventilation tube 1250. While the illustrated ventilation tube container 1200 includes a ventilation tube 1250 similar to that illustrated in FIG. 13A, any suitable ventilation tube can be used in combination with the ventilation tube container 1200, and skilled artisans will be able to select an appropriate ventilation tube for inclusion with a ventilation tube container according to a particular embodiment based on various considerations, including the intended use of the ventilation tube, and others.

Each recess 1204 includes a first portion 1210, a second portion 1220, and a third portion 1230. The first portion 1210 is configured to have a diameter slightly smaller than the outer diameter 1252 of the flange 1254 of the ventilation tube 1250 and a depth substantially equal to the distance between the proximal end of the flange 1254 and the proximal end of the frusto-conical section 1256 of the ventilation tube 1250. Alternatively, the first portion 1210 of each recess 1204 can be slightly larger than the outer diameter 1252 of the flange 1254 of the ventilation tube and include a liner, such as the foam insert 1212 illustrated in the figures. Foam insert assist with gripping the ventilation tube 1250 when it is housed within the ventilation tube container 1200. The foam insert 1212 can have a depth equal to, less than, or greater than, the depth of the first portion 1210 of the recess 1204. These configurations ensure that the ventilation tube 1250, which is formed of a compressible material, is snuggly retained within the recess 1204. While a foam insert has been described and illustrated, any suitable material can be used to facilitate gripping the ventilation tube when it is housed within the ventilation tube container, and skilled artisans will be able to select a suitable material according to a particular embodiment based on various considerations, including the type of ventilation tube being housing in the ventilation tube container, and the amount of grip desired.

The second portion 1220 extends from the first portion 1210 to the third portion 1230 and is configured to mirror the frusto-conical section 1256 of the ventilation tube 1250. The third portion 1230 extends from the second portion to the bottom of the recess and is configured to have a depth sufficient to allow the sharp distal end 1262 of the introducer 1260 to advance through the central channel 1258 of the ventilation tube 1250 and load the ventilation tube 1250 onto the introducer 1260. The depth of the recesses 1210, 1220, and 1230 will be slightly greater than the length of the introducer 1260 from the distal end 1262 to the bend or the distal end 1262 of the introducer 1260 to the distal end of the cannula.

While the recess 1204 has been described and illustrated as having a particular configuration, other configurations are considered suitable, and skilled artisans will be able to select a suitable configuration for the recess according to a particular embodiment based on various considerations, including the configuration of the ventilation tube, the configuration of the cannula, and the configuration of the introducer.

The ventilation tube container 1200 allows a user to load a ventilation tube 1250 onto a delivery system (e.g., introducer) without having to manually force the ventilation tube 1250 onto the end of the delivery system using opposing hands, which may reduce the risk of injury. In addition, the ventilation tube container 1200 aids with proper alignment of the ventilation tube 1250 when loaded onto a delivery system. Furthermore, the ventilation tube container 1200 advantageously allows a physician to reuse a delivery system and reload additional ventilation tubes 1250 on the delivery system, should more than one be needed.

While the ventilation tube container 1200 has been described as having independent recesses to house individual ventilation tubes 1250, the ventilation tube container 1200 can include a single elongated recess, with liner partition separating each ventilation tube, to house multiple ventilation tubes 1250. Alternatively, the liner, and/or liner partitions can be omitted. Furthermore, while multiple ventilation tubes 1250 have been described and illustrated as housed within the ventilation tube container 1200, the number of ventilation tubes 1250 included in the ventilation tube container 1200 can vary, and skilled artisans will be able to select a suitable number of ventilation tubes to include with a ventilation tube container according to a particular embodiment based on various considerations, including, the intended use of the ventilation tube, and the configuration of the ventilation tube. Examples of suitable numbers of ventilation tubes include one, two, three, four, five, six and any other number determined suitable for a particular application.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed is:

1. A delivery system comprising:
an introducer having a first proximal end and a first distal end;
a handle disposed on the first proximal end of the introducer and comprising a head member, a housing, and a finger retraction handle;
the head member disposed over the introducer and having a second proximal end, a second distal end, and a wall defining a lumen extending between the second proximal end and the second distal end;
the housing disposed over the introducer and having a third proximal end, a third distal end, and a wall defining an aperture and a cavity, the third distal end adapted to be attached to the second proximal end of the head member;
the aperture extending through the wall of the housing and providing access to the cavity, the aperture having a first opening and an opposably positioned second opening, the aperture containing a rocker arm;
the rocker arm pivotally attached within the aperture and having a first portion and an opposably positioned second portion;
the cavity in communication with the lumen of the head member and having a fourth proximal end and a fourth distal end, the cavity containing a drum and a spring;
the drum slidably disposed over the introducer and having a fifth proximal end and a fifth distal end;
the spring disposed between the fourth distal end of the cavity and the fifth distal end of the drum;
the finger retraction handle slidably disposed over the housing and having a sixth proximal end and a sixth distal end;
a cannula slidably disposed over the introducer and having a seventh proximal end, a seventh distal end, and an outside diameter, the seventh proximal end directly attached to the fifth distal end of the drum, the cannula moveable along the introducer between a first position and a second position;
a ventilation tube releasably disposed on the first distal end of the introducer, the ventilation tube having an eighth proximal end, an eighth distal end, and a wall defining a channel extending between the eighth proximal end and the eighth distal, the channel having a resting diameter and a loaded diameter;
wherein the outside diameter of the cannula is greater than the loaded diameter of the channel; and
wherein the first portion of the rocker arm extends through the first opening of the aperture and is disposed proximal to the sixth proximal end of the finger retraction handle, and the second portion of the rocker arm extends through the second opening of the aperture and is disposed proximal to the fifth proximal end of the drum.

2. The delivery system of claim 1, wherein the first distal end of the introducer defines a first introducer diameter; and
wherein the first introducer diameter is greater than the resting diameter of the ventilation tube.

3. The delivery system of claim 1, wherein the introducer defines a bend between the first proximal end and the first distal end.

4. The delivery system of claim 3, wherein the ventilation tube is disposed on the introducer distal to the bend.

5. The delivery system of claim 1, wherein the introducer is formed of a malleable material adapted to allow a user to bend the introducer to conform to actual or expected anatomy of a bodily passage.

6. The delivery system of claim 5, wherein the cannula is formed of a malleable material adapted to allow a user to bend the cannula to conform to actual or expected anatomy of a bodily passage.

7. The delivery system of claim 1, wherein the ventilation tube comprises a drug eluting material.

8. The delivery system of claim 7, wherein the drug eluting material comprises one of antithrombogenics, antiproliferatives, antibiotics, antivirals, antifungals, or anti-inflammatories.

9. The delivery system of claim 1, wherein the ventilation tube comprises a resorbable material.

10. The delivery system of claim 1, wherein the ventilation tube has a proximal flange.

11. The delivery system of claim 10, wherein the ventilation tube has a distal flange.

12. The delivery system of claim 11, wherein the distal flange of the ventilation tube is frusto-conical.

13. The delivery system of claim 1, wherein the introducer extends through the drum and the proximal end of the introducer is attached to the housing.

14. The delivery system of claim 1, wherein the cannula extends through the spring and the seventh proximal end is directly attached to the fifth distal end of the drum.

* * * * *